(12) United States Patent
Gorelick et al.

(10) Patent No.: US 10,918,493 B2
(45) Date of Patent: Feb. 16, 2021

(54) JOINT REPLACEMENT DEVICE

(71) Applicant: FIBIOSEQ MEDICAL LTD., Rosh-Hanikra (IL)

(72) Inventors: Lauren Gorelick, Rosh-Hanikra (IL); Ofer Vikinsky, Tzur Yigal (IL)

(73) Assignee: Fibioseq Medical Ltd., Rosh-Hanikra (IL)

( * ) Notice: Subject to any disclaimer, the term of this patent is extended or adjusted under 35 U.S.C. 154(b) by 35 days.

(21) Appl. No.: 15/888,094

(22) Filed: Feb. 5, 2018

(65) Prior Publication Data
US 2019/0240037 A1 Aug. 8, 2019

(51) Int. Cl.
*A61F 2/42* (2006.01)
*A61F 2/30* (2006.01)

(52) U.S. Cl.
CPC ........ *A61F 2/4261* (2013.01); *A61F 2/30749* (2013.01); *A61F 2/30756* (2013.01); *A61F 2002/3065* (2013.01); *A61F 2002/30429* (2013.01); *A61F 2002/30624* (2013.01); *A61F 2002/30655* (2013.01); *A61F 2002/30662* (2013.01); *A61F 2002/30841* (2013.01); *A61F 2002/4264* (2013.01); *A61F 2002/4269* (2013.01); *A61F 2002/4289* (2013.01); *A61F 2002/4292* (2013.01)

(58) Field of Classification Search
CPC .......... A61F 2/4261; A61F 2/42; A61F 2/583; A61F 2/28; A61F 2002/305; A61F 2002/3625; A61F 2002/365; A61F 2002/3652; A61F 2002/4627; A61F 2002/91566; A61F 2002/91591; A61F 2002/4051; A61F 2002/4085
See application file for complete search history.

(56) References Cited

U.S. PATENT DOCUMENTS

| 8,764,830 | B2 | 7/2014 | Robinson et al. |
| 9,717,599 | B1* | 8/2017 | Gorelick ............... A61F 2/4261 |
| 2008/0051909 | A1* | 2/2008 | Wolfe .................. A61F 2/4261 |
| | | | 623/21.12 |

FOREIGN PATENT DOCUMENTS

WO    WO 2017/153989    9/2017

OTHER PUBLICATIONS

International Search Report for PCT application No. PCT/IL2019/050105, dated Apr. 18, 2019.

* cited by examiner

*Primary Examiner* — Ann Schillinger
(74) *Attorney, Agent, or Firm* — Pearl Cohen Zedek Latzer Baratz LLP

(57) ABSTRACT

A joint replacement device includes a male component with a structure to couple to a bone on one side of a joint, and an outer articulation surface that is attached to the structure via a neck. A female component is configured to couple to a bone on an opposite side of the joint and includes a cavity that is surrounded by an inner articulation surface. An opening of the cavity is shaped to enable insertion of the outer articulation surface into the cavity when the outer articulation surface is aligned with the opening, and to prevent separation of the male component from the female component when rotated so as not to align with the opening. The neck is located within the opening and the outer articulation surface is rotatable within the outer articulation surface with a rotation that is limited by dimensions of the opening and the neck.

10 Claims, 22 Drawing Sheets

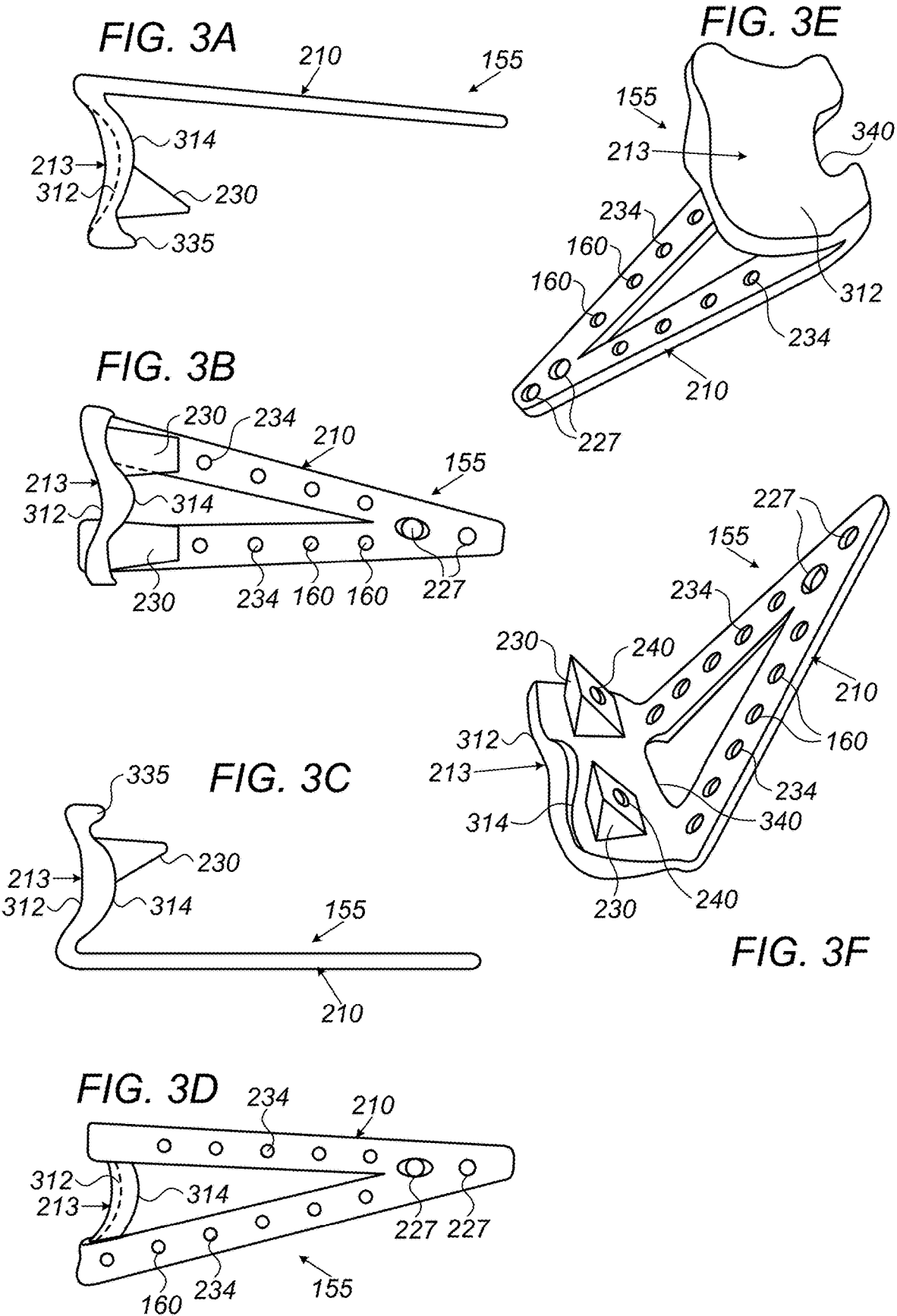

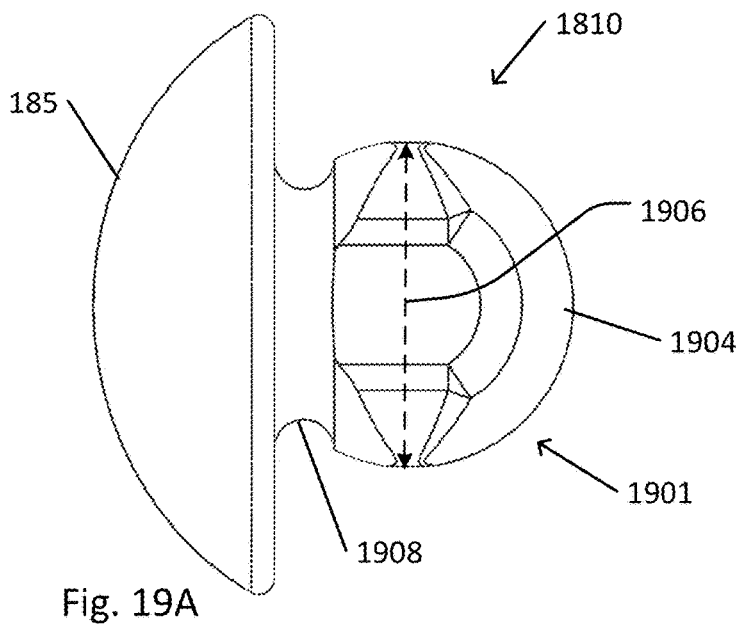
Fig. 19A
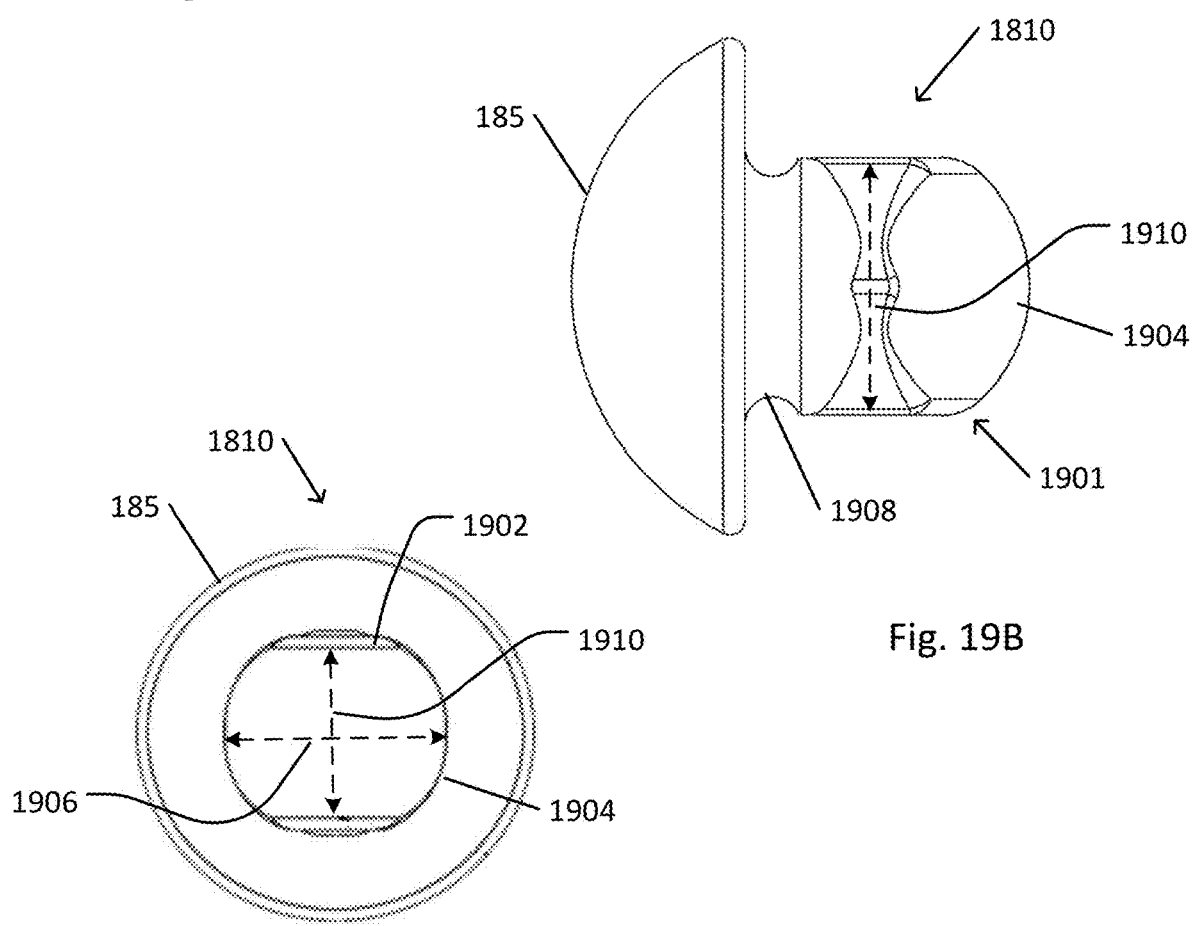
Fig. 19B
Fig. 19C

JOINT REPLACEMENT DEVICE

FIELD OF THE INVENTION

The present invention relates to replacement joints. More specifically, the present invention relates to a joint replacement device.

BACKGROUND OF THE INVENTION

The human wrist is a complex joint interface that bridges the proximal bones of the hands with the bones of the forearm known as the radius and ulna bones. The wrist includes a variety of carpal bones and multiple joints that intercommunicate in a common synovial cavity. These articulations work together to allow for a wide range of motion in the wrist joint. Most of the wrist motion occurs in the radiocarpal joint (RCJ) and the distal radioulnar joint (DRUJ).

The motion of the radiocarpal joint occurs between the radius and the first proximal row of carpal bones, which act together through the articular disc, and between the proximal and distal row of carpal bones. There is more a limited motion between the distal carpal bones and metacarpal bones in the hand. The DRUJ is a pivot joint located between the radius and ulna for supination and pronation movements of the hand.

Different wrist pathologies may occur in the wrist bones or joints resulting from conditions such as osteoarthritis, or from traumas, such as bone fractures, for example. A patient, or subject, with these wrist pathologies may experience severe pain during wrist movements ranging to severe disabilities due to limitations in wrist movements.

The wrist joint allows multi-axial movement with wide range of motion in all axes. In a healthy joint, the range of motion (ROM) for flexion-extension (bending of the hand in the direction of the palm or back of the hand) is almost 90 degrees in each direction, and between 20° and 30° for ulnar and radial lateral bending of the hand (e.g., in the direction of the thumb or little finger). The center of rotation (COR) in the physiological joint is not fixed. This floating quality of the center of rotation of the joint allows the joint to adjust to and remain stable in the face of large loads.

Commercially available artificial joints are typically designed to rotate around a fixed geometry of concave and convex surfaces, e.g., in the form of ball-and-socket joints. One reason for this is the engineering challenge of providing a wide range of motion under significant loads while minimizing wear of the artificial joint. The use of flexible materials to provide a floating COR may be problematic. Due to the complex biomechanics of the wrist joint, shear forces and linear stretching forces (that tend to separate the ball from the socket) are applied to the joint in the course of many common activities. The rigidity of the COR cannot accommodate or counter these shear and stretching forces, which may then lead to dislocation of the joint.

SUMMARY OF THE INVENTION

There is thus provided, in accordance with an embodiment of the present invention, a joint replacement device including: a male component including a structure configured to couple to a bone on one side of a joint between two bones, the male component including an outer articulation surface that is attached to the structure via a neck; and a female component configured to couple to a bone on an opposite side of the joint between two bones, the female component including a cavity, wherein the female component includes an inner articulation surface surrounding the cavity and configured to enable the outer articulation surface of the male component to rotate within the cavity, the cavity including an opening that is shaped to enable insertion of the outer articulation surface into the cavity through the opening when the outer articulation surface is aligned with the opening, and to prevent separation of the male component from the female component when the inserted outer articulation surface is rotated such that the outer articulation surface is not aligned with the opening, wherein after insertion of the outer articulation surface into the cavity, the neck is located within the opening and the outer articulation surface is rotatable within the outer articulation surface with a rotation that is limited by dimensions of the opening and the neck.

Furthermore, in accordance with an embodiment of the present invention, the outer articulation surface and the opening are each elongated, and the outer articulation surface and the opening are aligned when the long dimension of the outer articulation surface is parallel to the long dimension of the opening.

Furthermore, in accordance with an embodiment of the present invention, a diameter of the neck is selected to provide a predetermined range of motion of the replacement joint for longitudinal bending parallel to the long dimension of the opening.

Furthermore, in accordance with an embodiment of the present invention, a width of the opening and a diameter of the neck are selected to provide a predetermined range of motion of the replacement joint for lateral bending parallel to the width of the opening.

Furthermore, in accordance with an embodiment of the present invention, the outer articulation surface is substantially spherical with flattened opposite sides.

Furthermore, in accordance with an embodiment of the present invention, a projected length of the opening is longer than a diameter of the of the outer articulation surface.

Furthermore, in accordance with an embodiment of the present invention, a projected length of the opening is substantially equal to a diameter of the inner articulation surface.

Furthermore, in accordance with an embodiment of the present invention, the replacement joint is a wrist replacement joint.

Furthermore, in accordance with an embodiment of the present invention, the structure that is attached to the male component includes a convex head.

Furthermore, in accordance with an embodiment of the present invention, the female member includes a carpal bone insert for attaching to a carpal capitate member.

BRIEF DESCRIPTION OF THE DRAWINGS

In order for the present invention, to be better understood and for its practical applications to be appreciated, the following Figures are provided and referenced hereafter. It should be noted that the Figures are given as examples only and in no way limit the scope of the invention. Like components are denoted by like reference numerals.

FIG. 3A schematically illustrates a first side view of a radial member, in accordance with some embodiments of the present invention;

FIG. 3B schematically illustrates a bottom view of a radial member, in accordance with some embodiments of the present invention;

FIG. 3C schematically illustrates a second side view of a radial member, in accordance with some embodiments of the present invention;

FIG. 3D schematically illustrates a top view of a radial member, in accordance with some embodiments of the present invention;

FIG. 3E schematically illustrates a first perspective view of a radial member, in accordance with some embodiments of the present invention;

FIG. 3F schematically illustrates a second perspective view of radial member, in accordance with some embodiments of the present invention;

FIG. 19A schematically illustrates a side view of an asymmetric male component of the joint replacement device shown in FIG. 18A, the view showing the long axis of the male component;

FIG. 19B schematically illustrates a side view of the asymmetric male component shown in FIG. 19A, the view showing the short axis of the male component;

FIG. 19C schematically illustrates an axial view of the asymmetric male component shown in FIG. 19A;

DETAILED DESCRIPTION OF THE INVENTION

Figure 1:
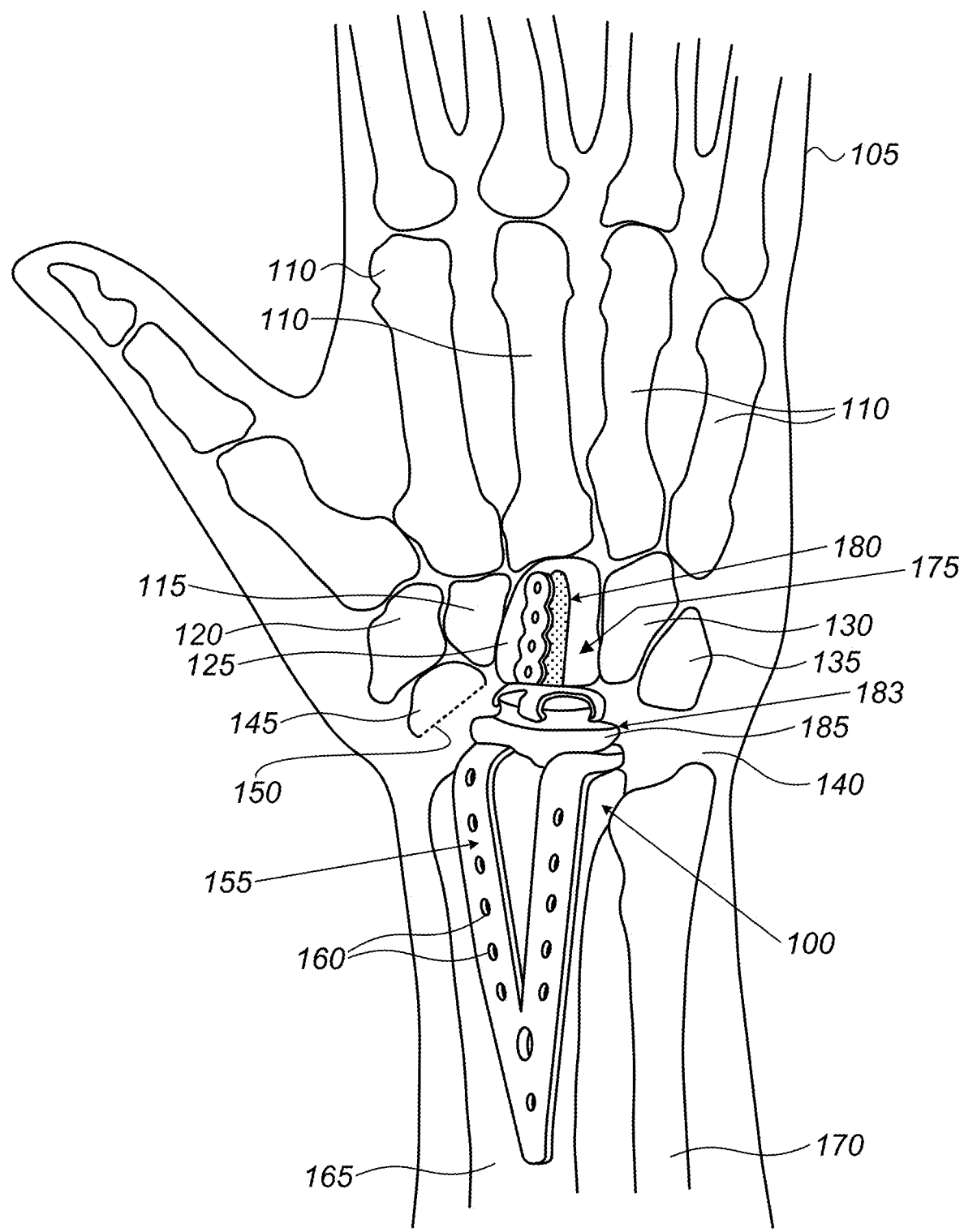
FIG. 1 schematically illustrates a dorsal view of a hand with a radiocarpal joint (RCJ) replacement, in accordance with some embodiments of the present invention.

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, use of the conjunction "or" as used herein is to be understood as inclusive (any or all of the stated options).

When severe wrist pathologies occur, therapeutic methods such as the use of medications may not alleviate the pain and movement limitations in the wrist joints for the patient. Partial or full wrist arthroplasty, or wrist joint replacements, may be the best course of treatment for the patient or subject.

Previously, different wrist implant topologies involved the resection of portions of the radius and/or ulna bones and affixing portions of the implant components, such as pegs, within the soft intramedullary canal. Such soft tissue stabilizing techniques of the implant components in the soft medullary tissue have been shown to loosen over time and ultimately fail, which requires additional surgery to fix and re-stabilize the implants. Moreover, in some implant topologies, the implant components may be bolted across multiple carpal bones to fix the multiple carpal bones in place severely limiting wrist movements. Some implants may bond portions of the radius to the ulna particularly in the case after large resections of those bones. These implant topologies severely limit the motion in the multiple wrist joints and may cause early loosening of the implant.

Described herein are some embodiments of a method and apparatus for wrist arthroplasty including radiocarpal joint (RCJ) and distal radioulnar joint (DRUJ) replacements. A method and apparatus for renewing the articular surface of the distal radius with a cartilage replacement can be used to repair damage, for example, from intra-articular fractures of the distal radius (e.g., from sport injuries) according to some embodiments of the present invention is also taught herein without the need to replace the entire joint (e.g., hemi-arthroplasty). Implant solutions according to some embodiments of the present invention overcome many of the implant failure and joint mobility problems seen in previous wrist implants and prostheses.

Wrist implants according to some embodiments of the present invention further account for minimal bone resection, preservation of the mobility of the radiocarpal, intercarpal and carpometacarpal joints, and a reduction of shear, bending and frictional forces in the implant components so as to prevent a loosening of the implant. Wrist implant topologies according to some embodiments of the present invention do not apply a classic ball and socket approach to the joint but rather apply methods of joint articular surface reconstruction to the complex joint surfaces. Implant technologies according to some embodiments of the present invention include wrist implant topologies which combine radiocarpal joint (RCJ) replacement with the option of DRUJ resurfacing replacement and stabilization within the same implant.

Implant topologies according to some embodiments of the present invention utilize a plate fixation method whereby the implant components are plate-like and use screws to affix the plate components to the hard, outer cortical bone layers for better implant stability. There is minimal bone resection with minimal placement of the implant components within the soft issue of the medullary cavity to stabilize the implant. Plate-like components used in some embodiments of the present invention employ a closed frame construction, such as the Y-plate affixed to the radius used in the RCJ implant as will described later, so as to achieve maximum contact and mechanical stability of the implant with prevention of implant failure. Surgical techniques employed according to some embodiments of the present invention for implanting the wrist replacements are simple and easy.

FIG. 1 schematically illustrates a dorsal view of a hand 105 with a first embodiment of a radiocarpal joint (RCJ) replacement 100, in accordance with some embodiments of the present invention. Hand 105 includes metacarpal bones 110, and the carpal bones, or carpus, including carpal trapezoid bone 115, carpal trapezium bone 120, carpal capitate bone 125, carpal hamate bone 130, and carpals triquetral/pisiform bones 135.

To implant the RCJ replacement shown in FIG. 1 in the wrist of hand 105, the carpal lunate bone is removed from a region 140 from hand 105. A carpal scaphoid bone 145 is surgically cut along a cut plane 150 and cartilage is removed from the RCJ. Radius bone 165 and ulna bone 170 are shown in FIG. 1.

A radial member 155 of the RCJ replacement includes holes 160 through which fasteners, typically screws, are to be inserted and threaded to allow affixing, attaching, or locking radial member 155 to a portion of an end of radius bone 165 proximal to the wrist. In contrast to the problems associated with soft tissue mounting of implants, radial member 155 is typically affixed to the cortex of radius bone 165 so as to provide a solid mechanical support for the RCJ replacement. A carpal bone insert 180 of the RCJ replacement is configured to be inserted and affixed only to carpal capitate bone 125 of the wrist, but not to other carpal bones, allowing greater maneuverability of the wrist, as a result. Carpal capitate bone insert 180 is coupled to a bulbous component 183, which includes a convex head 185 substantially opposite to carpal capitate bone insert 180.

Figure 2:
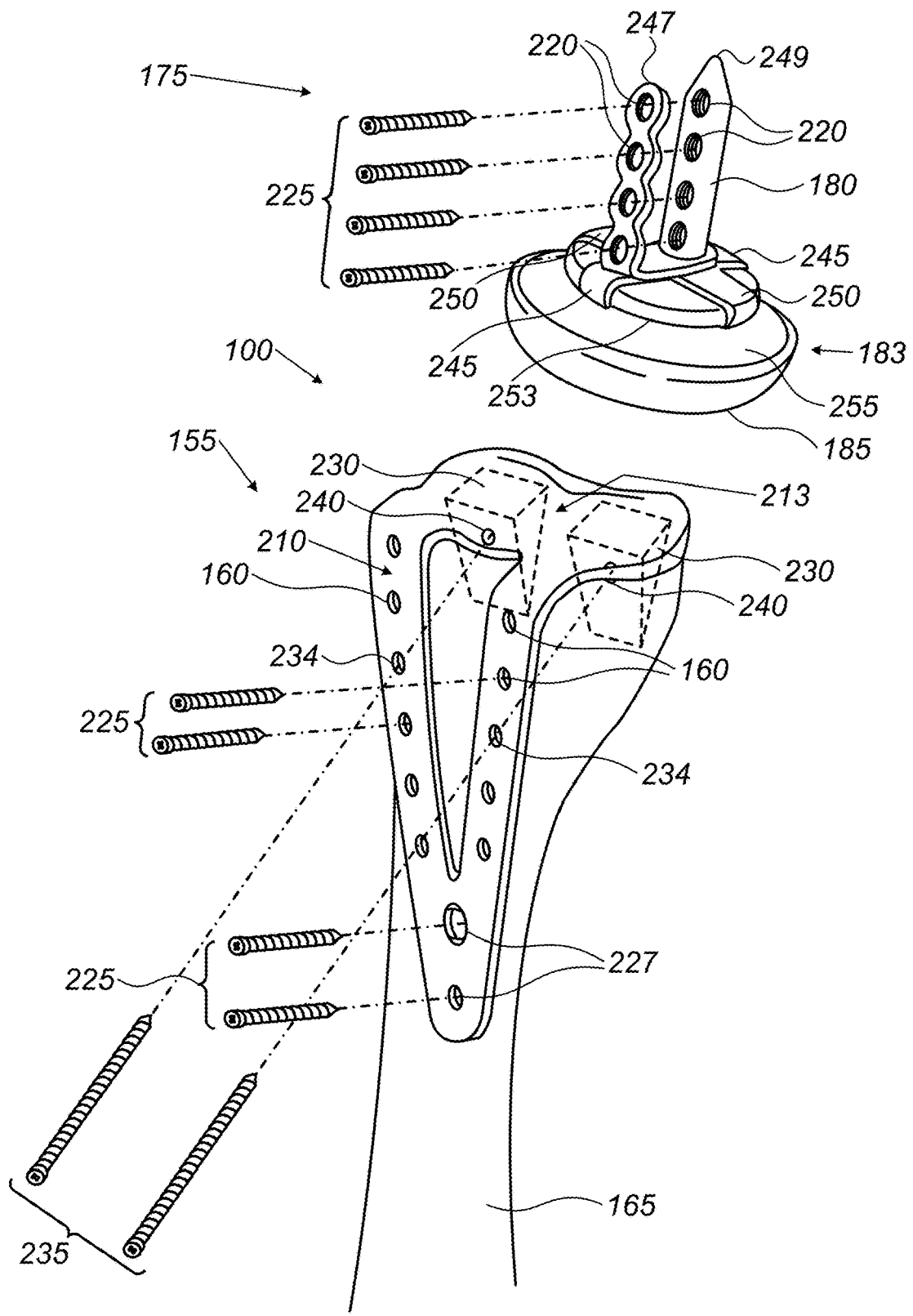
FIG. 2 schematically illustrates an exploded view of a radiocarpal joint (RCJ) replacement, in accordance with some embodiments of the present invention.

FIG. 2 schematically illustrates an exploded view of radiocarpal joint (RCJ) replacement 100, in accordance with some embodiments of the present invention. Radial member 155 of the radiocarpal joint (RCJ) replacement includes a radial fixture 210 to be affixed over a longitudinal aspect of the radial bone. Radial fixture 210 may have various forms, designed to match and provide good anchorage and coupling with the radius bone when attached to it. For example, radial fixture 210 may be V-shaped designed to present two joined bars that are to be affixed laterally onto radial bone 165.

Radial member 155 further includes a radial articular resurfacing plate 213 having a substantially smooth concave surface that is to be located at the end of the radial bone proximal to the wrist for supporting the radial member 155 when in-situ. The wrist includes the carpal bones and multiple joints that intercommunicate in a common synovial cavity. "Proximal" to the wrist refers, in the context of the present application, to the side of radial bone 165 nearest the carpal bones. This portion of the radial bone is referred to, in the context of the present application, as the distal radius. Radial articular resurfacing plate 213 is attached substantially perpendicular to V-shaped radial fixture 210 as shown in FIG. 2.

Carpal capitate bone insert 180 includes a dorsal surface cortical plate 247 and a central intraosseous stem 249. A bulbous component 183 is configured to be flexibly coupled to carpal capitate bone insert 180 and located substantially opposite to carpal capitate bone insert 180. Bulbous component 183 includes a convex head 185 having a convex surface. Dorsal cortical plate 247 is maneuvered, during the implantation procedure, to be positioned on the dorsal cortical position of carpal capitate bone 125 and stem 249 is inserted into the central intraosseous position of the carpal capitate bone. Four screw holes 220 for four screws 225 are located on both stem 249 and plate 247 of insert 180. Four screws 225 traverse carpal capitate bone 125 in the dorsal to palmar direction so as to affix plate 247 to carpal capitate bone 125 and central intraosseous stem 249; however, any number screws may be used.

The head of stem 249 includes several petals, in this example, four petals. Two petals 245 are generally oriented in the dorsal-volar direction and two petals 250 are generally oriented in the radioulnar direction. The petals are flexibly configured to snap-in, or connect to a neck 253, so as to hold bulbous component 183 to carpal capitate bone insert 180.

Radial articular resurfacing plate 213 of radial member 155 with the concave surface is configured to be operably coupled to the convex surface of convex head 185 of carpal capitate member 175 so as to allow radial freedom of motion of carpal capitate member 175 with respect to radial articular resurfacing plate 213 after implantation. Note that the term "operably coupled" in the context of wrist arthroplasty is defined herein to mean that in coupling, bonding, connecting or otherwise holding together the two components forming the wrist joint replacement, implant, or prostheses, with two articulating surfaces, the motion of the two articulating surfaces are identical, or most closely replicate, the same motions found in equivalent in vivo joint articulating surfaces. Stated differently by way of example, the movements, or motions, of the RCJ replacement after implantation would most closely replicate the same movements, or motions, found equivalently in a normal (healthy) radiocarpal joint in the wrist.

Radial fixture 210 (the dorsal plate), includes holes 160 through which fasteners, typically screws 225, are used for plate fixation of radial member 155 to the radial bone cortex. This technique for assembling the RCJ replacement is referred to, in the context of the present application, as dorsal radius fracture fixation. In some embodiments, holes 160 have threading for screws 225 to be fixed to radial member 155. One or more holes 227 on the central region of the "V" pass are oval shaped. Screwing screw 225 into a chosen side of oval hole 227 applies a longitudinal stress to fixture 210 in the direction of the chosen side so as to allow an additional degree of freedom for placing and fastening radial fixture 210 to radius bone 215. Although a V-shaped radial fixture is described, aimed at providing good mechanical stability, other shapes may be considered, too. The V-shape is not in any way limiting the embodiments of the present invention to that shape. Other shapes for the radial fixture may be used with varying number of screws and respective screw holes in any geometric orientation.

Radial fixture 210 (dorsal plate) is also connected to radial articular resurfacing plate 213. Two triangular pegs 230 that are formed in the bottom side of radial articular resurfacing plate 213 are designed to be pressed against and penetrate into the end of the radius bone as shown in FIG. 2, for enhanced stability. Triangular pegs 230 also include holes 240. Screws 235 may be screwed through obliquely threaded screw holes 234 formed in radial fixture 210 (e.g., dorsal plate). Screw holes 234 are not on the same lateral position along both side of fixture 210 so as to compensate for the shapes of radial bone 165 and the end of radial bone 165 (e.g., the radial articular surface). Screws 235 pass through radius bone 165 to threaded screw holes 235 and 240 at an oblique angle of about 43 degrees with the bottom surface of radial articular resurfacing plate 213 opposite radius bone 165. Fastening screws 235 are used for affixing radial member 155 via pegs 230 of the radiocarpal joint (RCJ) replacement to radial bone 165, which forms a mechanically stable pyramid-like closed frame, enhancing self-support.

FIG. 3A schematically illustrates a first side view of radial member 155, in accordance with some embodiments of the present invention.

FIG. 3B schematically illustrates a bottom view of radial member 155, in accordance with some embodiments of the present invention.

FIG. 3C schematically illustrates a second side view of radial member 155, in accordance with some embodiments of the present invention.

FIG. 3D schematically illustrates a top view of radial member 155, in accordance with some embodiments of the present invention.

FIG. 3E schematically illustrates a first perspective view of radial member 155, in accordance with some embodiments of the present invention.

FIG. 3F schematically illustrates a second perspective view of radial member 155, in accordance with some embodiments of the present invention.

Radial member 155 of the radiocarpal joint (RCJ) replacement includes a radial fixture 210 which is integrally formed with radial articular resurfacing plate 213. Radial articular resurfacing plate 213 is concave 312 toward the carpus, or carpal bones, and convex 314 toward the radial articular surface of the radial bone according to the normal anatomical concavity of the articular surface of the distal radius. In some embodiments, radial articular resurfacing plate 213 with concave surface 312 is fabricated or formed to present a highly polished metal surface. Convex surface 314 may be coated (e.g., hydroxylapatite) for better contact with the distal radius bone and also to allow for bone growth.

Radial fixture 210 also includes holes 160 for screws to affix the radial member 155 to the cortex of the radius and an oval hole 227 which allows another longitudinal degree of freedom in firmly attaching radial fixture 210 to the radius bone as described in FIG. 2. The volar ridge of plate 213 (e.g., side of plate 213 proximal to the palm of the subject's hand) includes a volar hook 335. Volar hook 335 increases the stability of radial articular resurfacing plate 310 mounted on to the end of the radius bone proximal to the wrist.

Two triangular pegs 230 are formed in convex surface 314 of radial articular resurfacing plate 213 (e.g., on the volar portion of plate 213). Pegs 230 have screw holes 240 such that two lock screws 235 mounted through holes 240 and holes 234 (as described in FIG. 2) formed in radial fixture 210 prevent a rotation of radial articular resurfacing plate 213. Radial articular resurfacing plate 213 has a deltoid notch 340 so as to accommodate Lister's tubercle and the bone joint capsule.

Figure 4A:
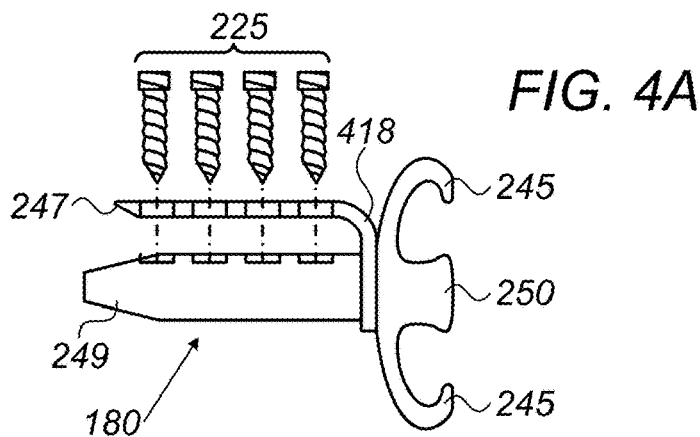
FIG. 4A schematically illustrates a side view of a carpal capitate bone insert, in accordance with some embodiments of the present invention.

FIG. 4A schematically illustrates a side view of carpal capitate bone insert 180, in accordance with some embodiments of the present invention. When implanting carpal capitate bone insert 180, central intraosseous stem 249 is inserted and implanted into the central intraosseous position of the carpal capitate bone. Dorsal cortical plate 247 is maneuvered, during the implantation procedure, to be positioned on the dorsal cortical position of carpal capitate bone 125.

Four screw holes 220 for four screws 225 are located on both stem 249 and plate 247 of insert 180. Four screws 225 traverse and are threaded through carpal capitate bone 125 in the dorsal to palmar direction so as to affix plate 247 to carpal capitate bone 125 and central intraosseous stem 249; however, any number screws may be used. Holes 220 in plate 247 are parallel to holes 220 in stem 249. Plate 247 is connected to stem 249 at a proximal end 418 of stem 249. Also connected to a proximal end 418 of stem 249 are four petals. Two petals 245 are oriented in the dorsal-volar direction and two petals 250 are oriented in the radioulnar direction.

In some embodiments, carpal capitate bone insert 180 may be formed from titanium or stainless steel. In other embodiments, stem 249 are prepared with plasma deposited hydroxylapatite which gives stem 249 a corrugated coated surface for better bone growth and adhesion when stem 249 is implanted within the central intraosseous position of the carpal capitate bone.

Figure 4B:
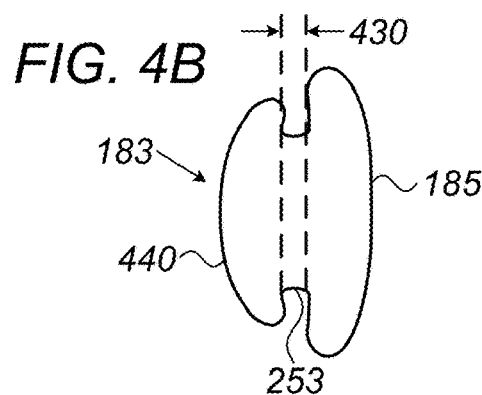
FIG. 4B schematically illustrates a side view of a bulbous component, in accordance with some embodiments of the present invention.

FIG. 4B schematically illustrates a side view of bulbous component 183, in accordance with some embodiments of the present invention. Bulbous component 183 includes a first convex head 440 and (second) convex head 185 (as described previously in FIGS. 1-2), substantially opposite each other and connected by neck 253 defining an annular groove 430 between first convex head 440 and second convex head 185.

Figure 4C:
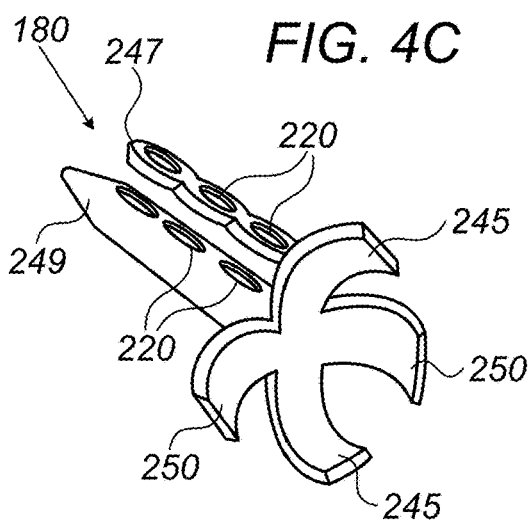
FIG. 4C schematically illustrates a perspective view of a carpal capitate bone insert, in accordance with some embodiments of the present invention.

FIG. 4C schematically illustrates a perspective view of carpal capitate bone insert 180, in accordance with some embodiments of the present invention.

Figure 4D:
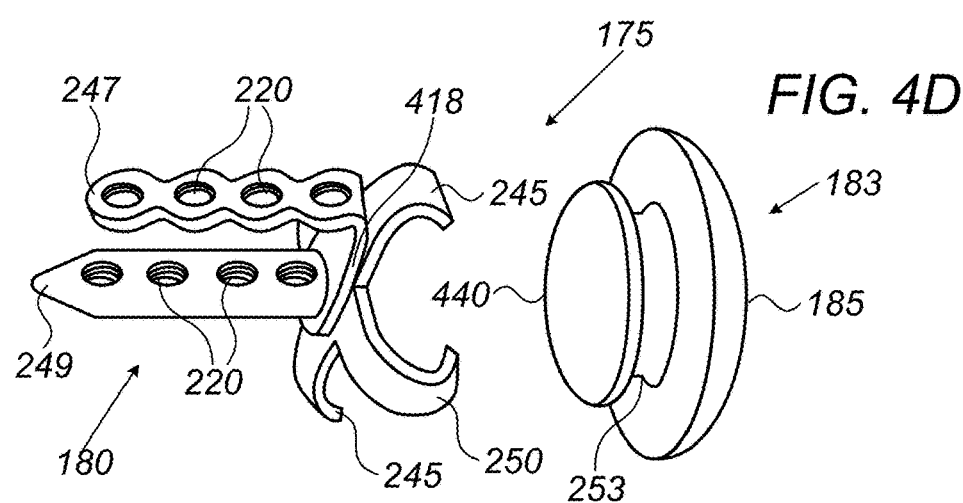
FIG. 4D schematically illustrates a top view of a carpal capitate bone insert and a bulbous component, in accordance with some embodiments of the present invention.

FIG. 4D schematically illustrates a top view of carpal capitate bone insert 180 and bulbous component 183, in accordance with some embodiments of the present invention. The four petals are substantially flexible and are configured to snap into annular ring 430 of neck 253 of bulbous component 183. Thus, the petals squeeze, hold, or bite on neck 253 of the bulbous component under pressure, which affixes carpal capitate bone insert 180 to bulbous component 183. However, since the petals are flexible, small deviations in motion up to 4 mm in any direction between central intraosseous stem 249 and first convex head 440 of bulbous component 183 may occur. Thus, in this context of the present application, the carpal capitate bone insert 180 is configured to be flexibly coupled to first convex head 440 of the bulbous component. A carpal capitate member may be defined herein as to include carpal capitate bone insert 180 flexibly coupled to bulbous component 183.

According to some embodiments of the invention, there may be provided bulbous components with different neck sizes to cater for various palm sizes. Bulbous component 183 may be made from a material selected from the group consisting of polyethylene, pyrocarbon, and ceramic. Similarly, the bulbous components may be provided with second convex heads 185 of different sizes. However, the size of second convex heads 185 is typically the same or similar for most purposes. The size of the carpal capitate member and can be predetermined by snapping in a bulbous component, for example, having the proper neck size to suit the patient's palm size. The adjustment of the size of the carpal capitate member in this manner can be used to balance between the tension and wrist motion during implantation so as optimize performance of the RCJ replacement.

The RCJ replacement effectively has two joints that can move during the motion of the RCJ wrist replacement. Movement in the first joint in the RCJ replacement mainly occurs where the convex surface of second convex head 185 is configured to be operably coupled to radial articular resurfacing plate 213. The area of the convex head articulates with the radial articular resurfacing plate of substantially the same area. In addition, the flexible coupling between carpal capitate bone insert 180 and bulbous component 183 forms a second flexible joint with another degree of freedom in the movement of the overall RCJ replacement. The flexible movements possible in the second joint are small relative to the large radial movements in the first joint.

Figure 5:
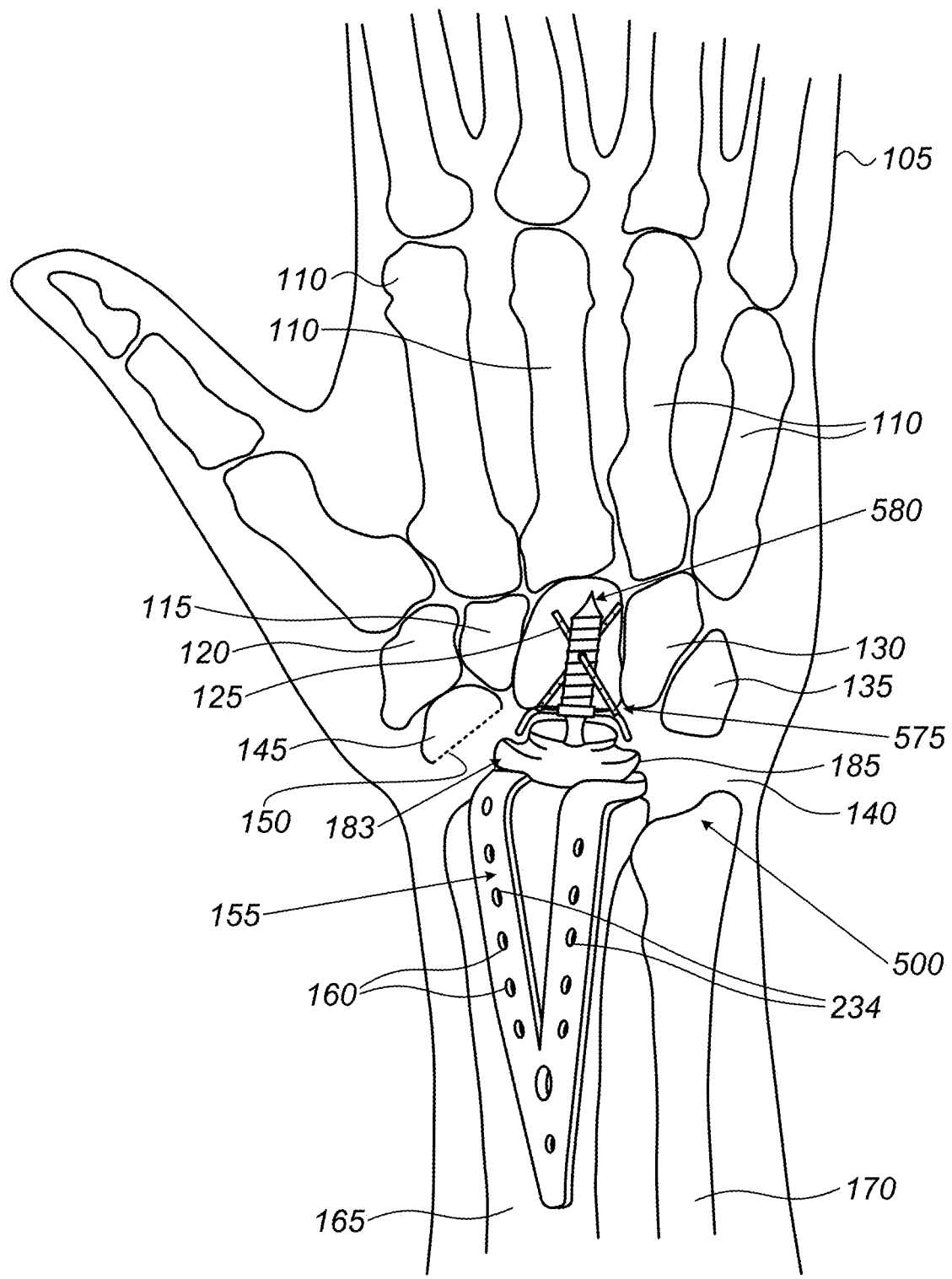
FIG. 5 schematically illustrates a dorsal view of a hand with a radiocarpal joint (RCJ) replacement, in accordance with some embodiments of the present invention.

FIG. 5 schematically illustrates a dorsal view of hand 105 with radiocarpal joint (RCJ) replacement 500, in accordance with some embodiments of the present invention. Dorsal view 500 of hand 105 includes metacarpal bones 110, and the carpal bones, or carpus, including carpal trapezoid bone 115, carpal trapezium bone 120, carpal capitate bone 125, carpal hamate bone 130, and carpals triquetral/pisiform bones 135.

In order for the RCJ replacement in the second embodiment of FIG. 5 to be implanted in the wrist of hand 105, first the carpal lunate bone is removed from a region 140 from hand 105. A carpal scaphoid bone 145 is surgically cut along a cut plane 150 and cartilage is removed from the RCJ. Radius bone 165 and ulna bone 170 are shown in FIG. 5.

A radial member 155 of the RCJ replacement includes radial member holes 160 through which fasteners, typically screws can be inserted and threaded to allow affixing or locking radial member 155 to a portion of an end of radius bone 165 proximal to the wrist. In contrast to soft tissue mounting of implants, radial member 155 is typically affixed to the cortex of radius bone 165 to provide a solid mechanical support for the RCJ replacement. A carpal capitate bone insert 575 of the RCJ replacement is configured to be affixed by a screw 580 only to carpal capitate bone 125 of the wrist but not to other carpal bones, allowing greater maneuverability of the wrist as a result. The head of screw 580 includes a spherical highly polished small head. In the same manner, as described in FIG. 4, carpal capitate bone insert 575 is flexibly coupled to bulbous component 183 with convex head 185.

Figure 6:
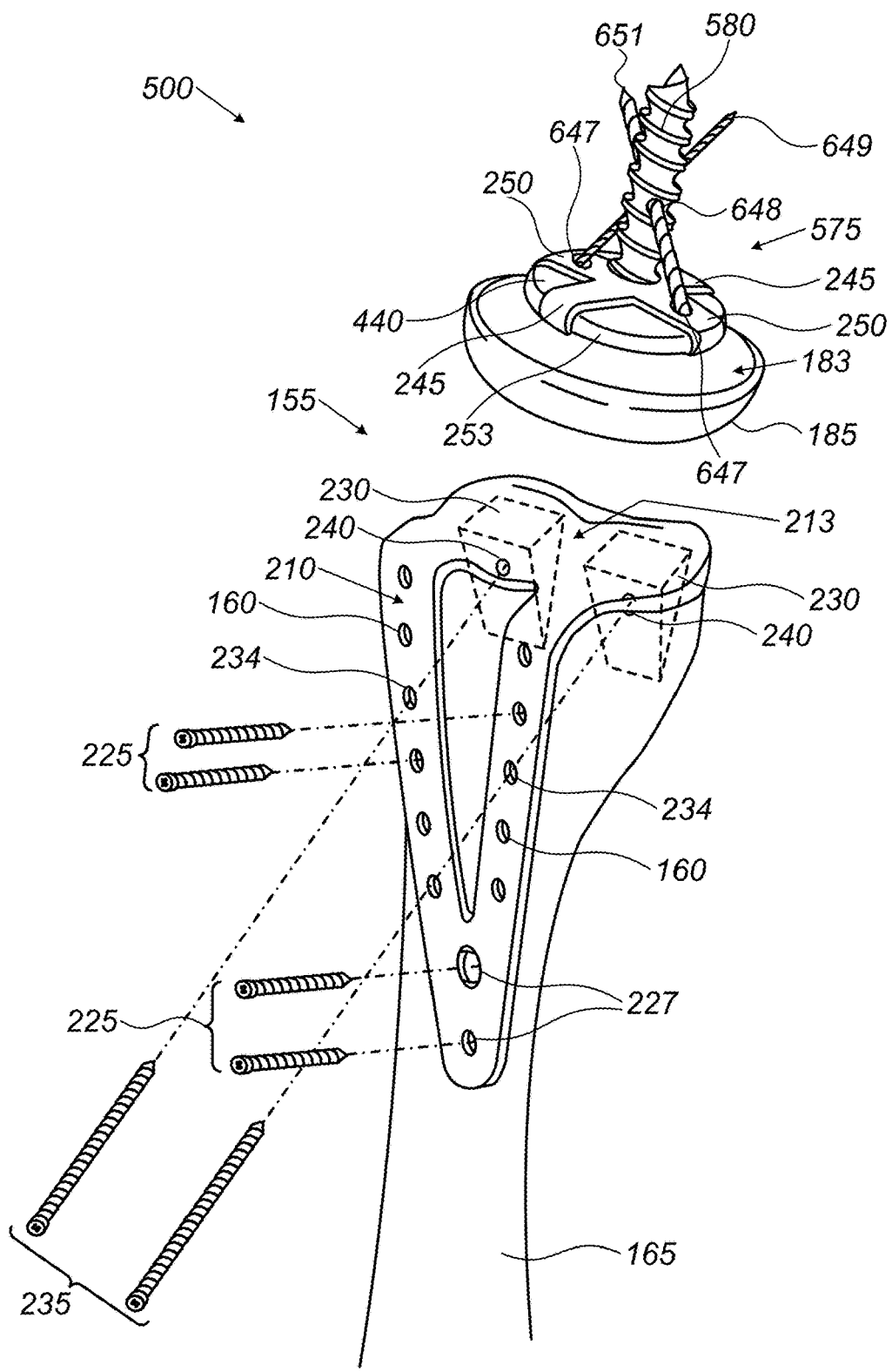
FIG. 6 schematically illustrates an exploded view of a radiocarpal joint (RCJ) replacement, in accordance with some embodiments of the present invention.

FIG. 6 schematically illustrates an exploded view 600 of a radiocarpal joint (RCJ) replacement, in accordance with some embodiments of the present invention. A radial member 155 of the radiocarpal joint (RCJ) replacement includes a radial fixture 210 in the shape of a "V" which affixed the radial member laterally onto radial bone 165 and radial articular resurfacing plate 213 having a substantially smooth concave surface located at the end of the radial bone proximal to the wrist. Radial articular resurfacing plate 213 is attached at a nearly 90 degree angle to V-shaped radial fixture 210 as shown in FIG. 6.

Carpal capitate bone insert 575 includes screw 580 with wide threads along the shank which is inserted, threaded, implanted, or affixed to the carpal capitate bone. The head of screw 580 includes four petals. Two petals 245 are oriented in the dorsal-volar direction and two petals 250 are oriented in the radioulnar direction. The petals are configured to be connected to a neck 253 of bulbous component 183. Two petals 250 oriented in the radioulnar direction each have threaded oblique holes 647.

After implantation of the screw into the carpal capitate bone, two locking screws are threaded through the carpal capitate bone, through channels 648 formed in the shank of main capitate screw 580 and into oblique holes 647. A first locking screw 649 is mounted from threaded oblique hole 647 and is oriented toward the ulnar dorsal base of the carpal capitate bone. A second locking screw 651 is mounted from threaded oblique hole 647 and is oriented toward the radial volar base of the carpal capitate bone. The shank of screw 580 is coated for good contact and good bone growth with plasma deposited hydroxylapatite for implantation within the central intraosseous position of the carpal capitate bone.

Stated differently, in some embodiments, carpal capitate insert includes an implant insertion element selected from the group consisting of stem 249 and screw 580. The implant insertion element is implanted into the central intraosseous position of the carpal capitate bone and may be coated with hydroxylapatite.

Bulbous component 183 includes a convex head 185 having a convex surface. The four petals 245 and 250 are substantially flexible and allow the insertion of bulbous component 183 such that the four petals squeeze and bite down on annular ring 430 of neck 253 as described in FIG. 4 so as to affix the bulbous component to the carpal capitate bone insert. Applying bulbous components with different neck sizes, for example, allows for adjusting the size of carpal capitate member (e.g., bone insert 575 and bulbous component 183) as described for the embodiment shown in FIG. 4 so as to balance between the tension and wrist motion during implantation.

Radial articular resurfacing plate 213 of radial member 155 with the concave surface is configured to be operably coupled to the convex surface of convex head 185 of carpal capitate member 575 so as to allow radial freedom of motion of carpal capitate member 575 with respect to radial articular resurfacing plate 213 after implantation. The area of the convex surface of convex head 185 is substantially the same as the area of radial articular resurfacing plate 213.

Radial fixture 210, or dorsal plate, includes holes 160 through which fasteners, typically screws 225, are used for plate fixation of radial member 155 to the radial bone cortex. This technique for assembling the RCJ replacement may also be referred to as dorsal radius fracture fixation. In some embodiments, holes 160 have threading for screws 225 to be fixed to radial member 155. Two or three holes 227 on the central region of the "V" are oval which allow compression of radial fixture 210 longitudinally to radius bone 165.

Radial fixture 210 (dorsal plate) is also connected to radial articular resurfacing plate 213. Two triangular pegs 230 that are formed in the bottom side of radial articular resurfacing plate 213 are designed to be pressed against and penetrate into the end of the radius bone as shown in FIG. 2, for enhanced stability. Triangular pegs 230 also include holes 240. Screws 235 may be screwed through obliquely threaded screw holes 234 formed in radial fixture 210 (e.g., dorsal plate). Screw holes 234 are not on the same position along fixture 210 so as to compensate for the shapes of radial bone 165 and the end of radial bone 165 (e.g., the radial articular surface). Screws 235 pass through radius bone 165 to threaded screw holes 240 at an oblique angle of about 43 degrees with the bottom surface of radial articular resurfacing plate 213 opposite radius bone 165. Fastening screws 235 are used for affixing radial member 155 via pegs 230 of the radiocarpal joint (RCJ) replacement to radial bone 165, which forms a mechanically stable pyramid-like closed frame, enhancing self-support.

Figure 7:
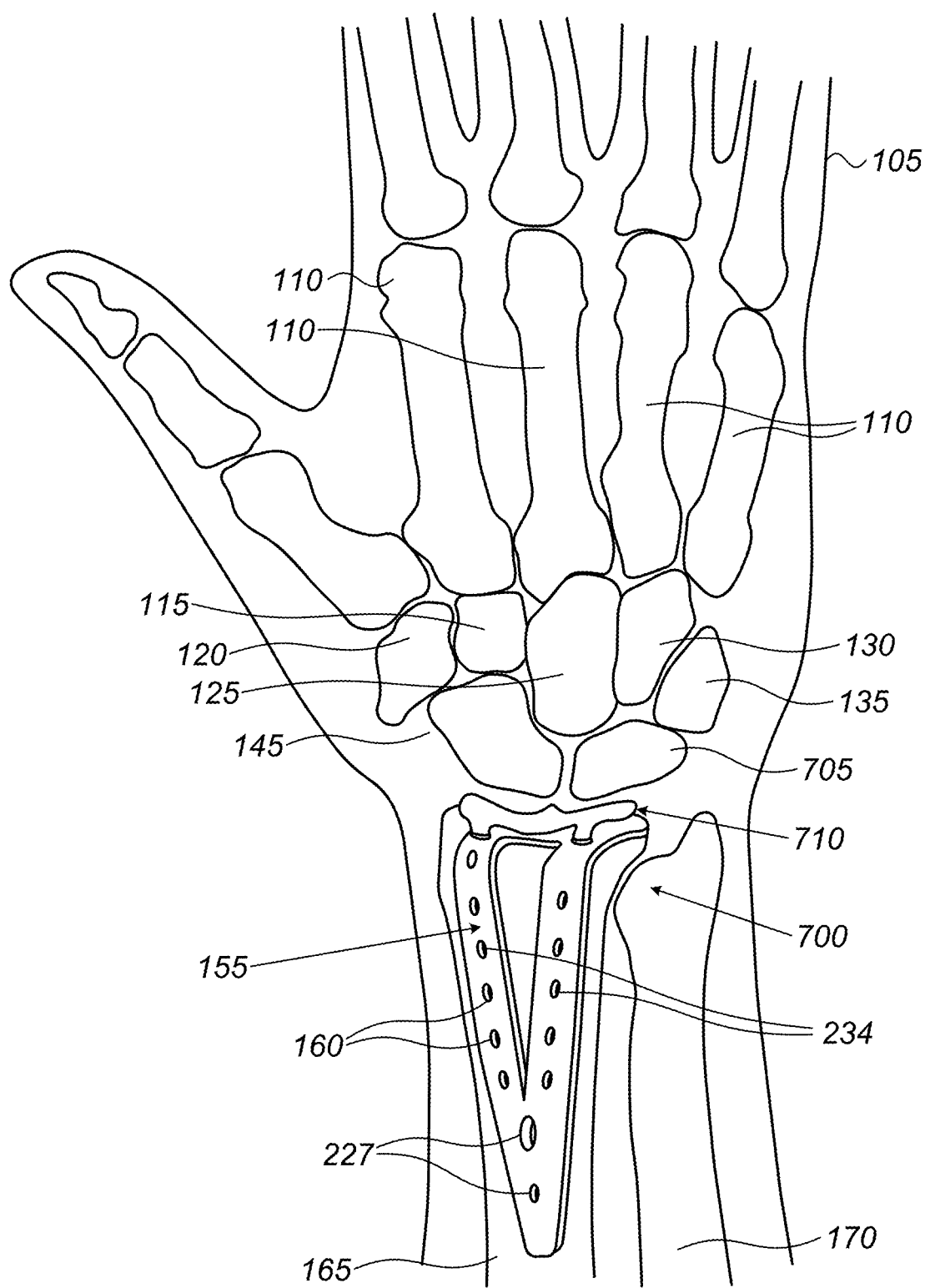
FIG. 7 schematically illustrates a dorsal view of a hand with a radiocarpal joint (RCJ) cartilage replacement, in accordance with some embodiments of the present invention.

FIG. 7 schematically illustrates a dorsal view of hand 105 with a radiocarpal joint (RCJ) cartilage replacement 700, in accordance with some embodiments of the present invention. The wrist bones shown in FIG. 7 are identical to that of FIG. 1 with the exception that carpal scaphoid bone 145 is not surgically cut and the carpal lunate bone 705 is not removed as described previously for the RCJ joint replacement. Here, all of the carpal bones are present. In the event of a sports injury where cartilage in the RCJ joint is fractured or damaged, the damaged cartilage is removed. However, a plastic cartilage replacement 710 is inserted and attached to radial member 155. The carpal bones are operably coupled to cartilage replacement 710 on a first side proximal to the wrist (e.g., to the carpal bones) so as to restore normal wrist motion after the RCJ cartilage was removed. The second side of cartilage replacement 710 is affixed to radial member 155.

Figure 8:
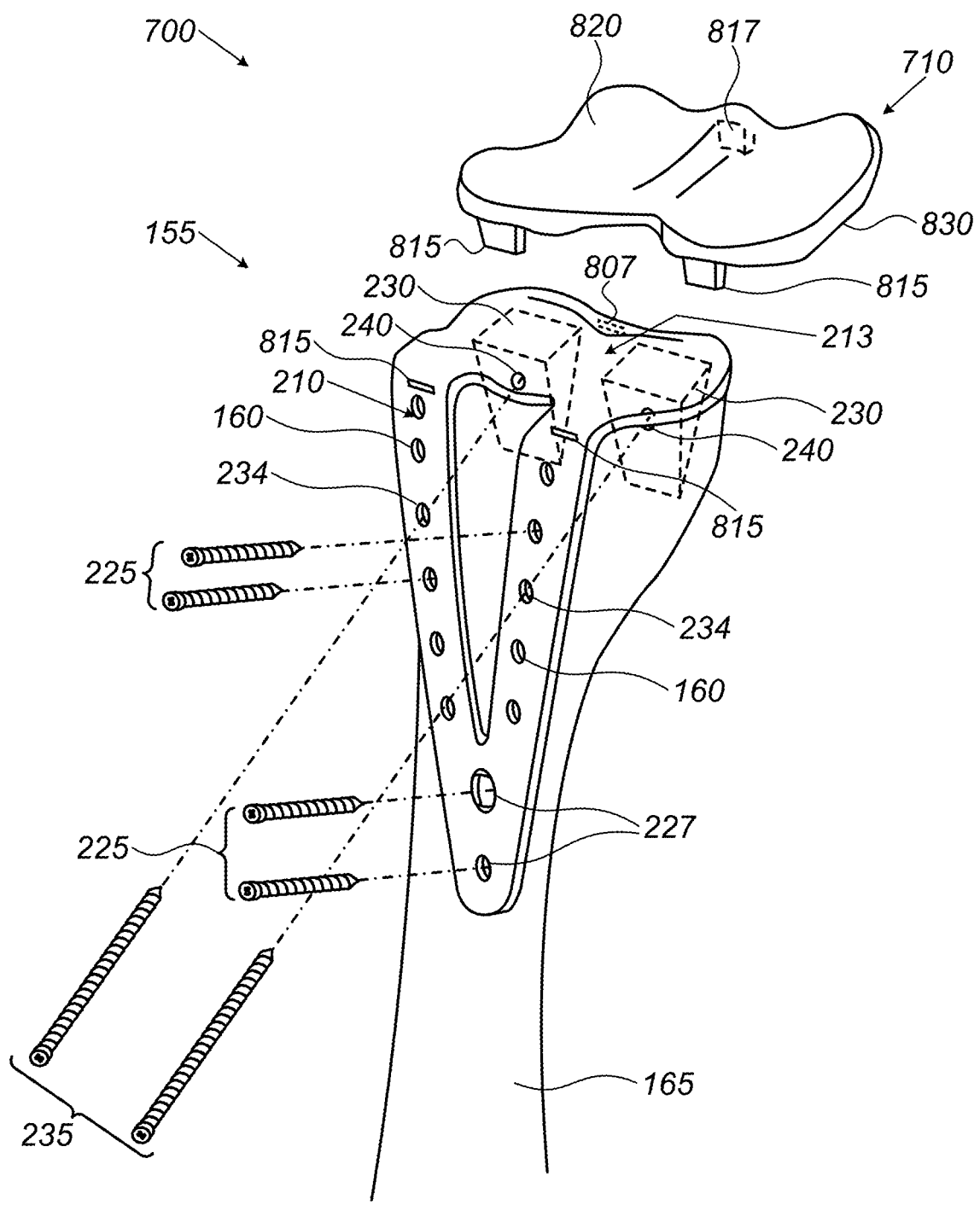
FIG. 8 schematically illustrates an exploded view of a radiocarpal joint (RCJ) cartilage replacement, in accordance with some embodiments of the present invention.

FIG. 8 schematically illustrates an exploded view of radiocarpal joint (RCJ) cartilage replacement 700, in accordance with some embodiments of the present invention. Radial member 155 is affixed to a portion of an end of radial bone 165 proximal to the wrist (e.g., the carpal bones of the wrist) by the same procedures described in the embodiments shown in FIGS. 1-6. However, radial member 155 also includes tab holes 805 and 807 which are configured to receive tabs 815 and 817 respectively that are formed on side 830 of cartilage replacement 710 proximal to radial member 155. In this manner, second side 830 of cartilage replacement 710 is affixed to radial member 155. Along a first side 820 of cartilage replacement 710, the carpal bones are operably coupled to of cartilage replacement 710, such that the wrist with cartilage replacement 710 can substantially exhibit the same motions as a normal (healthy) wrist.

Figure 9A:
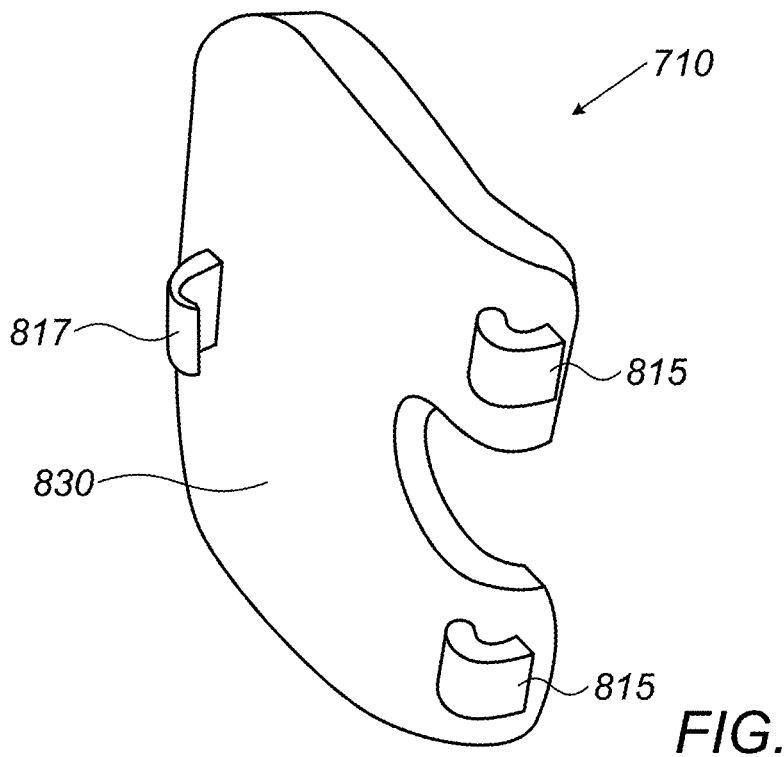
FIG. 9A schematically illustrates a bottom view of a cartilage replacement, in accordance with some embodiments of the present invention.

FIG. 9A schematically illustrates a bottom view of cartilage replacement 710, in accordance with some embodiments of the present invention. The bottom view of cartilage replacement 710 shows tabs 815 and 817 formed in side 830 (e.g., the second side affixed to radial member 155).

Figure 9B:
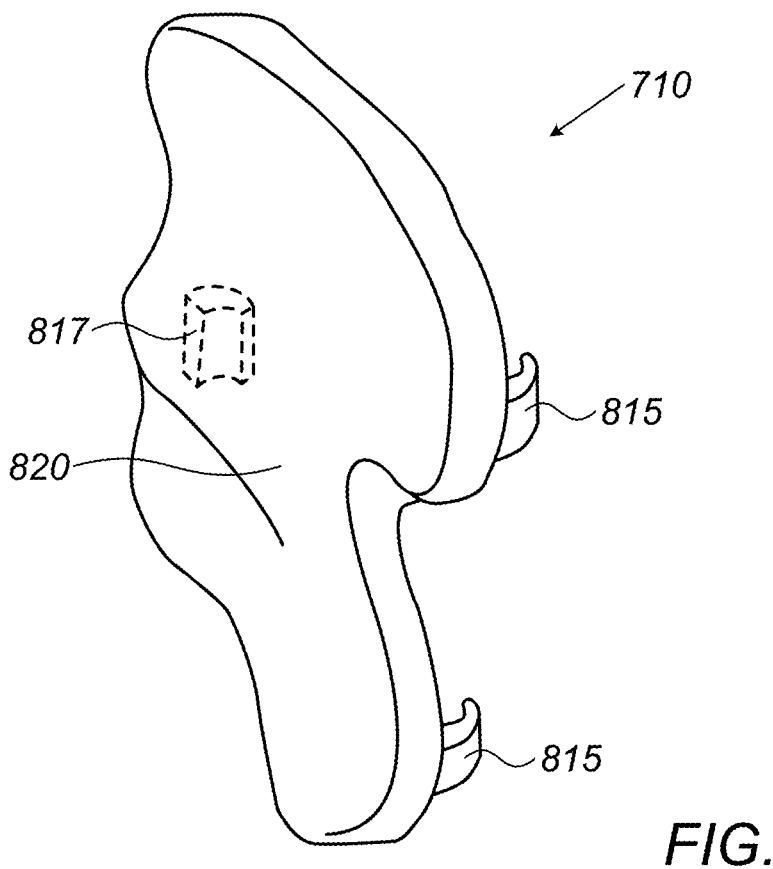
FIG. 9B schematically illustrates a top view of a cartilage replacement, in accordance with some embodiments of the present invention.

FIG. 9B schematically illustrates a top view of cartilage replacement 710, in accordance with some embodiments of the present invention. The top view of cartilage replacement 710 shows concave surface 820 (e.g., the first surface). In some embodiments, the plastic of concave surface 820 is machined and polished with optimal concavity to be operably coupled to the carpal bones in the wrist, such as for example, optimized to articulate with carpal scaphoid 145 and carpal lunate 705 (see FIG. 7).

When pathologies exist in the distal radioulnar joint (DRUJ), such as sigmoid notch damage, that affect supination and pronation movements of the wrist, a DRUJ replacement can be implanted to alleviate the dysfunction.

Figure 10:
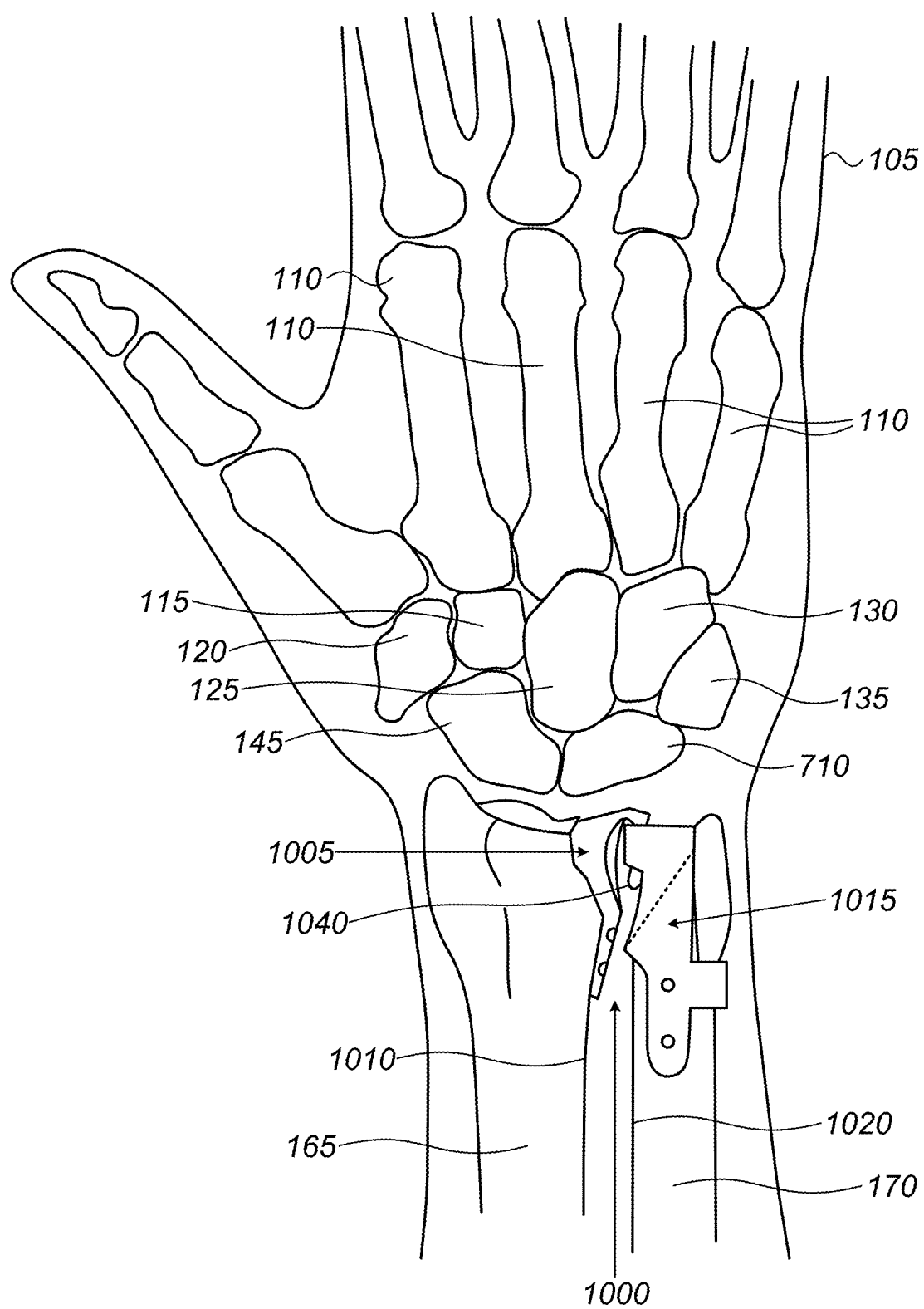
FIG. 10 illustrates a dorsal view of a hand with a distal radioulnar joint (DRUJ) replacement, in accordance with some embodiments of the present invention.

FIG. 10 illustrates a first dorsal view of hand 105 with a distal radioulnar joint (DRUJ) replacement 1000, in accordance with some embodiments of the present invention. A sigmoidal member 1005 is affixed to an ulnar side 1010 of radius bone 165 proximal to the wrist, or the bones in the wrist. An ulnar member 1015 is affixed to a radial side 1020 of ulna bone 170 and proximal to the wrist bones. Sigmoidal member 1005 also includes a hook 1040 which is inserted and held in ulnar member 1015 such that sigmoidal member 1005 is configured to be operably coupled to ulnar member 1015 so as to facilitate supination and pronation movement of the wrist and provide DRUJ stability.

Figure 11:
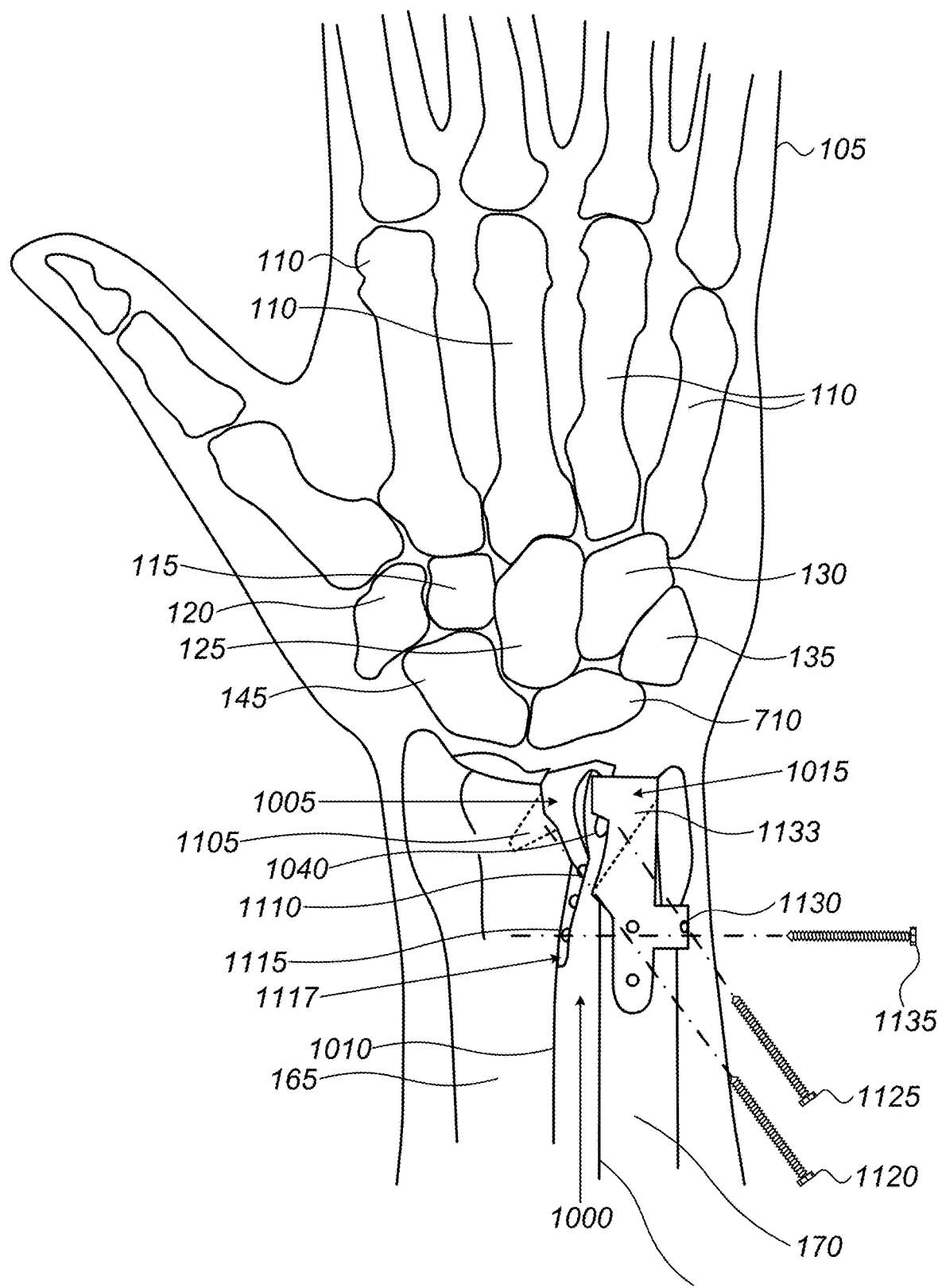
FIG. 11 schematically illustrates a dorsal view of a hand with a distal radioulnar joint (DRUJ) replacement, in accordance with some embodiments of the present invention, showing the direction of applying screws in fixing the DRUJ in position.

FIG. 11 schematically illustrates a second dorsal view of hand 105 with distal radioulnar joint (DRUJ) replacement 1000, in accordance with some embodiments of the present invention. Sigmoidal member 1005 includes a triangular peg 1105 that includes a threaded hole (not shown). Triangular peg 1105 is impacted, implanted, pressed, or hammered into the cancellous bone of the distal radius. Sigmoidal member 1005 is affixed to the distal radius by a screw 1120 that is inserted into a screw hole 1110 and is threaded into a screw hole (not shown) in triangular peg 1105. Similarly, a lower mounting bracket 1117 of sigmoidal member 1005 is affixed to radius bone 165 along ulnar side 1010 by a screw 1135 which is threaded into a screw hole 1115. Lower mounting bracket 1117 is affixed over a longitudinal aspect of the radial bone. This closed frame construction provides stability and dissipates forces across sigmoidal member 1005, which is similar to the topology for affixing radial member 155.

Ulnar member 1015 is also constructed with a triangular block 1133 that restores a partial oblique resection of the articular surface of an ulnar head 1140 of ulna bone 170, restoring nearly ⅔ of the ulnar head. Ulnar member 1015 is partially affixed by a screw 1125 inserted to threaded through screw hole 1130 into triangular block 1133.

Figure 12:
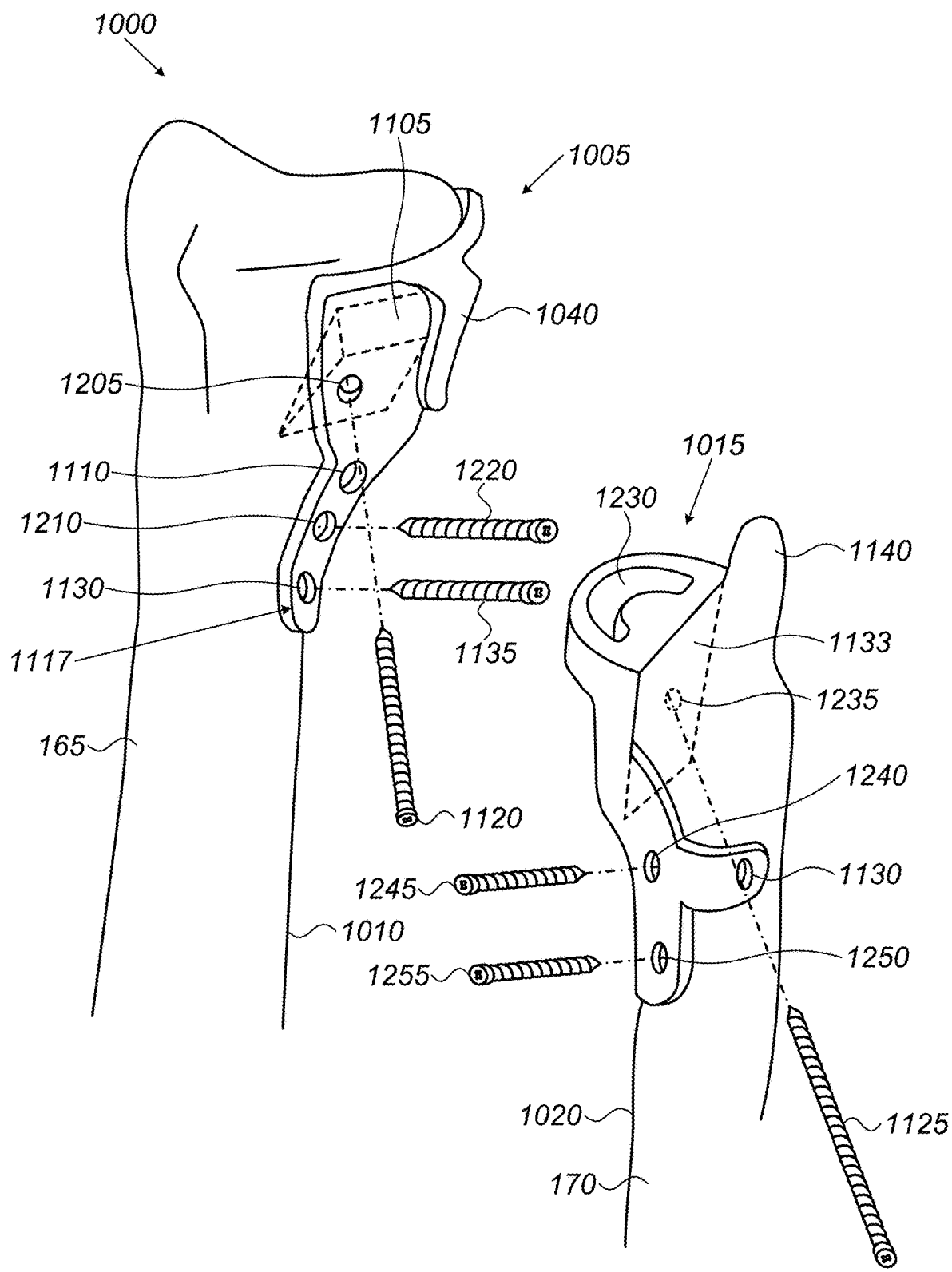
FIG. 12 schematically illustrates an exploded view of a distal radioulnar joint (DRUJ) replacement, in accordance with some embodiments of the present invention.

FIG. 12 schematically illustrates an exploded view of distal radioulnar joint (DRUJ) replacement 1000, in accordance with some embodiments of the present invention. Sigmoidal member 1005 includes hook 1040. After peg 1105 is impacted into the distal radius bone as described previously, sigmoidal member 1005 is affixed to the radius bone 165 by three screws. Screw 1120 is threaded obliquely through hole 1110 through the radial head into a threaded hole 1205 in peg 1105. Lower mounting bracket 1117 of sigmoidal member 1005 is affixed to radius bone 165 along ulnar side 1010 by screw 1135 threaded into screw hole 1115, and a screw 1220 threaded into a screw hole 1210.

A bore 1230 is formed into ulnar portion 1015. Bore 1230 may also be referred to herein as a supination-pronation tunnel. In some embodiments, bore 1230 may include a track formed in ulnar portion 1015. In other embodiments, bore 1230 may include a groove formed in ulnar portion 1015. Ulnar portion 1015 is held to ulna bone 170 by three screws as shown in FIG. 12. Screw 1125 is inserted obliquely into threaded hole 1130 crosses the resected portion of the ulna head and is threaded into a hole 1235 in triangular block 1133. The lower portion of the ulnar member is affixed to ulna bone 170 by two screws 1245 and 1255 in threaded screw holes 1240 and 1250, respectively. Threaded screw holes 1240 and 1250 may also have oval holes which can be provide axial compress of the ulnar member along the ulna bone.

Hook 1040 of sigmoidal member 1005 is inserted and held in bore 1230 in ulnar member 1015 which is configured to receive hook 1040 and to retain the hook after implantation. Although bore 1230 is shaped like a "C", as the C-shape has been determined to provide good stability of the DRUJ replacement when the wrist is moved in pronation and supination, any suitable bore shape can be chosen so as to optimize the joint stability and performance.

Figure 13A:
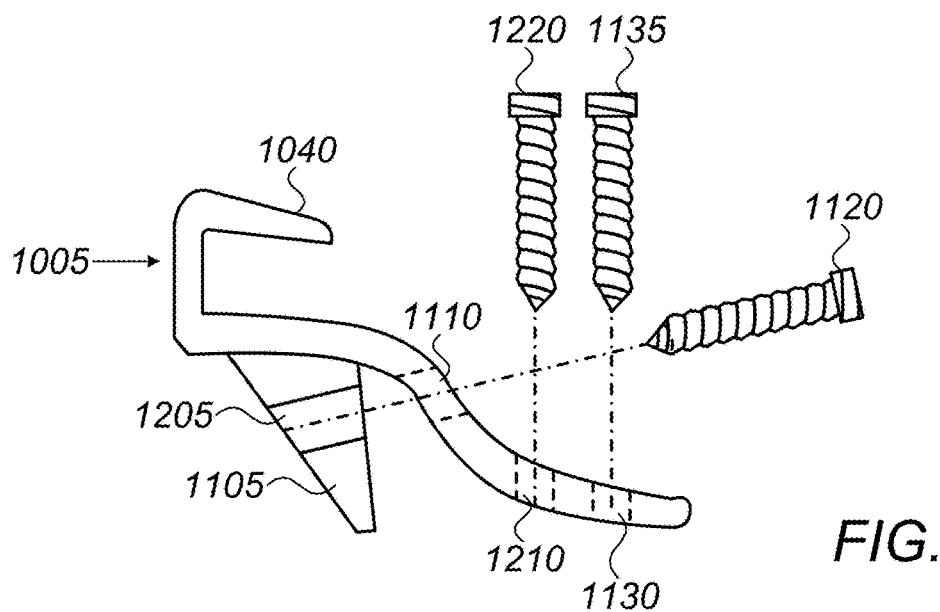
FIG. 13A schematically illustrates a side view of a sigmoidal member with a hook, in accordance with some embodiments of the present invention.

FIG. 13A schematically illustrates a side view of sigmoidal member 1005 with hook 1040, in accordance with some embodiments of the present invention.

Figure 13B:
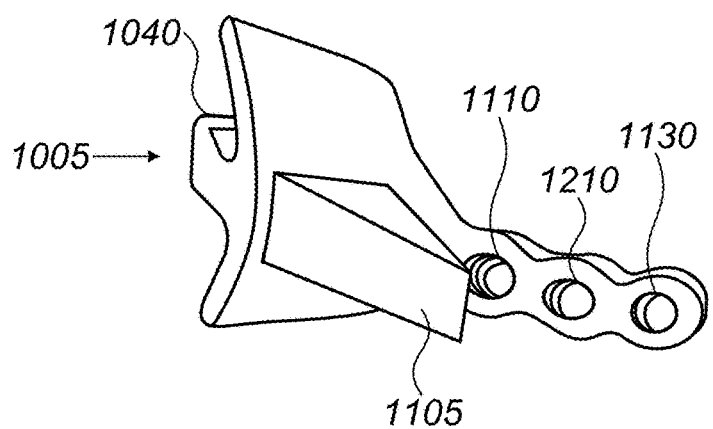
FIG. 13B schematically illustrates a top view of a sigmoidal member with a hook, in accordance with some embodiments of the present invention.

FIG. 13B schematically illustrates a top view of sigmoidal member 1005 with hook 1040, in accordance with some embodiments of the present invention.

Figure 13C:
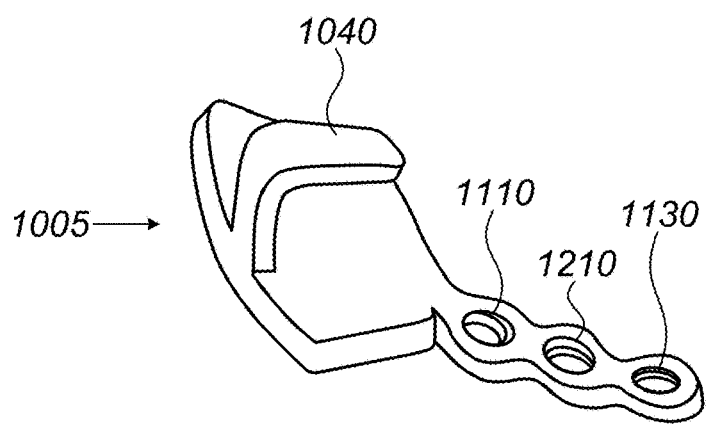
FIG. 13C schematically illustrates a bottom view of a sigmoidal member with a hook, in accordance with some embodiments of the present invention.

FIG. 13C schematically illustrates a bottom view of sigmoidal member 1005 with hook 1040, in accordance with some embodiments of the present invention.

Peg 1105 is impacted into the cancellous bone of the distal radius and affix to radius 165 by screw 1120 that is threaded through holes 1110 and 1205. The screws and screw holes may be the same as described in FIGS. 10-12. Sigmoidal member 1005 may be formed from polished stainless steel or titanium.

Figure 14A:
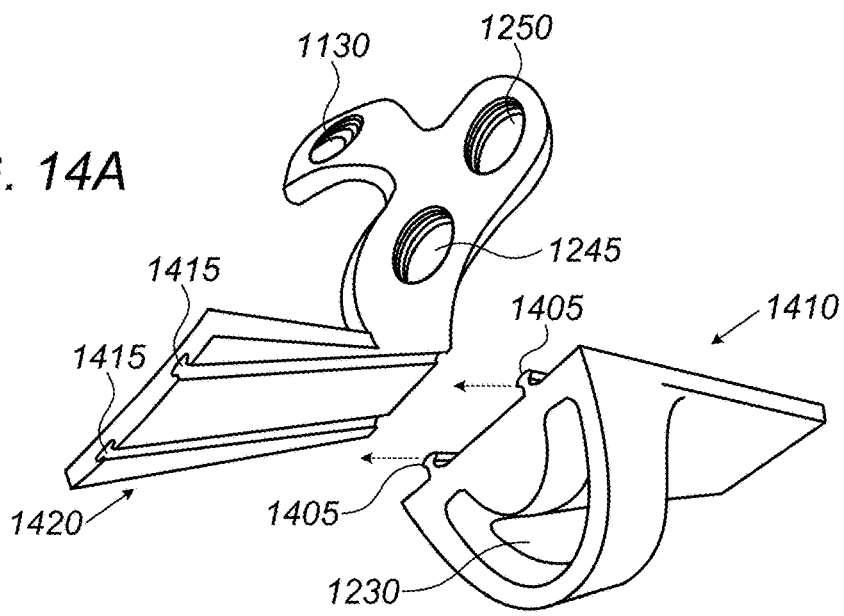
FIG. 14A schematically illustrates an exploded view of an ulnar member with a bore, in accordance with some embodiments of the present invention.

FIG. 14A schematically illustrates an exploded view of ulnar member 1015 with bore 1230, in accordance with some embodiments of the present invention.

Figure 14B:
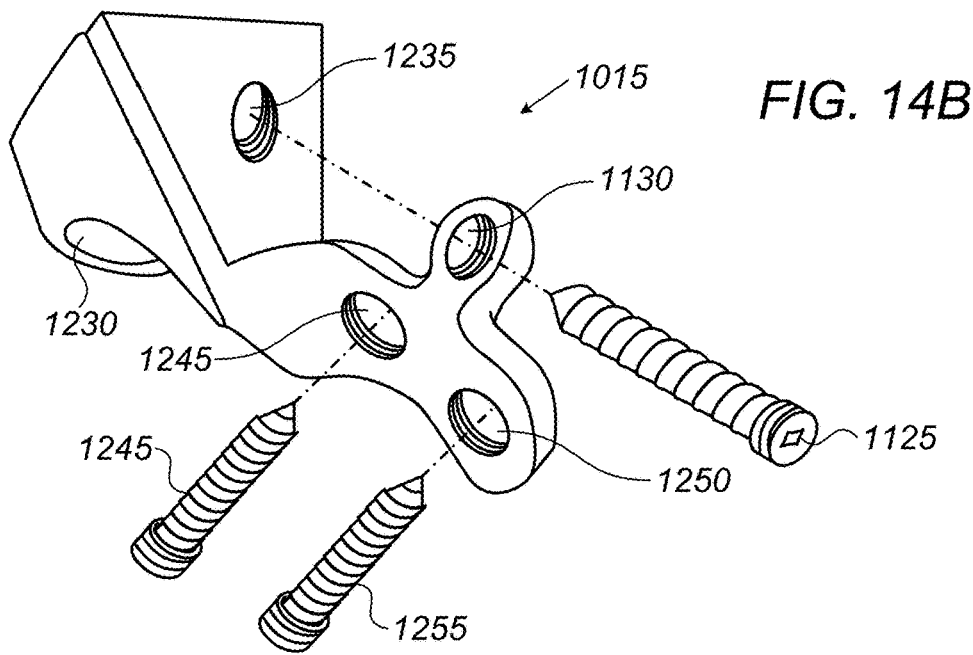
FIG. 14B schematically illustrates a first perspective view of an ulnar member with a bore, in accordance with some embodiments of the present invention.

FIG. 14B schematically illustrates a first perspective view of ulnar member 1015 with bore 1230, in accordance with some embodiments of the present invention.

Figure 14C:
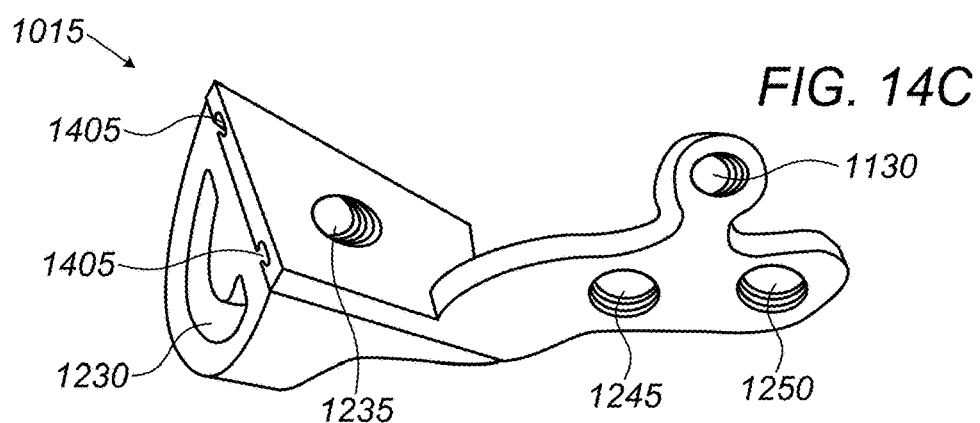
FIG. 14C schematically illustrates a second perspective view of an ulnar member with a bore, in accordance with some embodiments of the present invention.

FIG. 14C schematically illustrates a second perspective view of ulnar member 1015 with bore 1230, in accordance with some embodiments of the present invention.

As shown in FIG. 14A, ulnar member 1015 may be formed from two separate pieces: a receptacle piece 1410 and a mounting piece 1420. Receptacle piece 1410 includes two rails 1405. Bore 1230 is formed in receptacle piece 1410 and is configured to receive hook 1040. Mounting piece 1420 includes the screw holes used for affixing the ulnar member to the ulna bone and also includes tracks 1415 into which rails 1405 can be slid so as to hold receptacle piece 1410 on mounting piece 1420. In this manner, receptacle piece 1410 may be adjusted to have different overall lengths. Receptacle piece 1410 with different sizes or shapes of bore 1230 may also be used to optimize the performance of the DRUJ replacement. The screws and screw holes are the same as described in FIGS. 10-12. Receptacle piece 1410 is formed from a material selected from the group consisting of mobile polyethylene and pyrocarbon. Mounting piece 1420 is formed from a material selected from the group consisting of stainless steel and titanium. In some embodiments, the stainless steel and titanium may be impregnated with hydroxylapatite.

Figure 15:
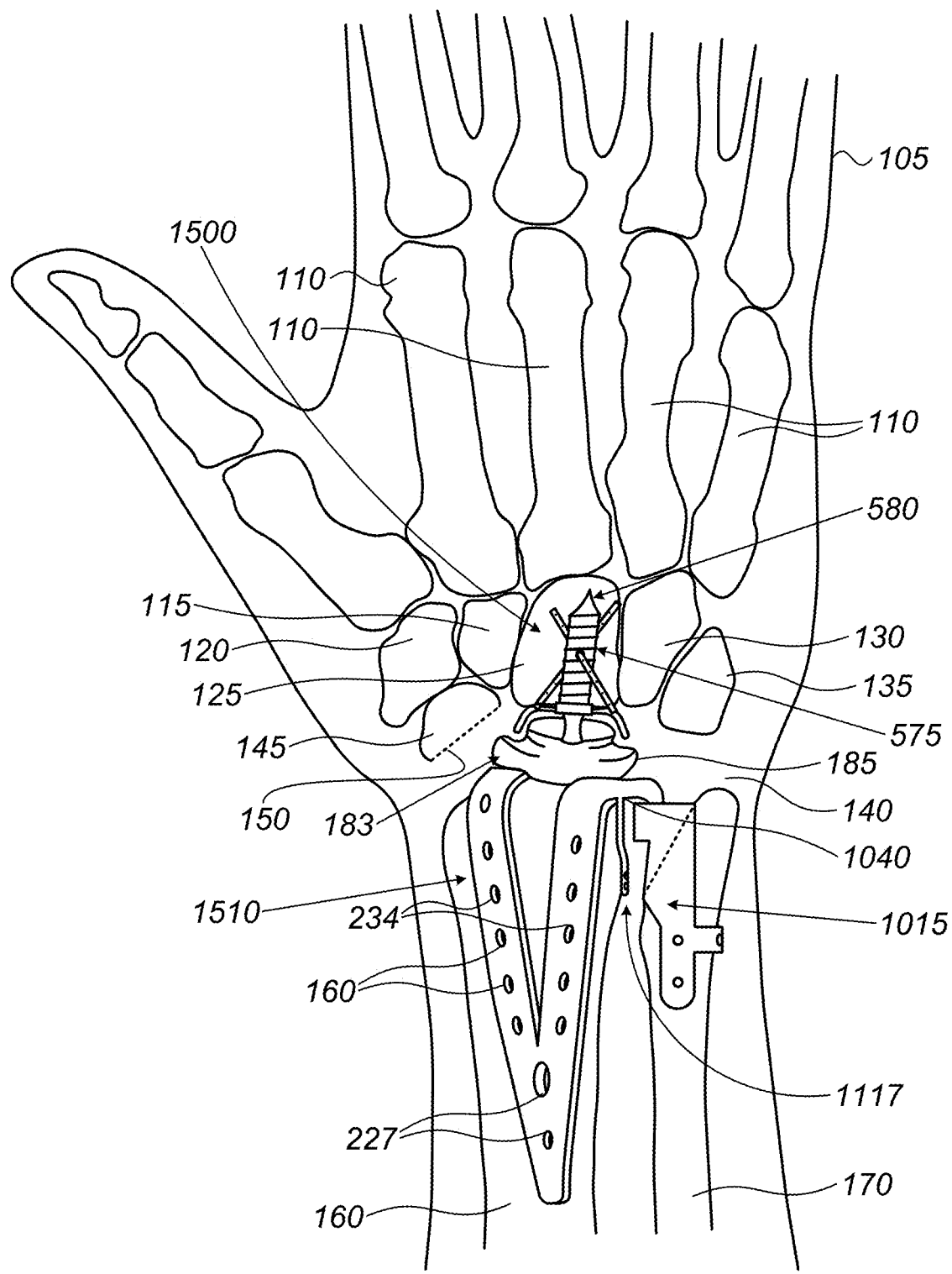
FIG. 15 schematically illustrates a dorsal view of a hand with a combination of a radiocarpal joint (RCJ) replacement and a distal radioulnar joint (DRUJ) replacement, in accordance with some embodiments of the present invention.

FIG. 15 schematically illustrates a dorsal view of hand 105 with a combination 1500 of a radiocarpal joint (RCJ) replacement and a distal radioulnar joint (DRUJ) replacement, in accordance with some embodiments of the present invention. In the event that the subject, or patient, requires both a RCJ and DRUJ replacement, the embodiments shown in FIGS. 5 and 10 may be combined as shown in FIG. 15. The description as to how the various members are affixed to the carpal capitate, radial and ulna bones as described previously. However, radial member 155 is modified to include the elements of the sigmoidal member, namely hook 1040 and lower mounting bracket 1117 of sigmoidal member 1005.

Figure 16:
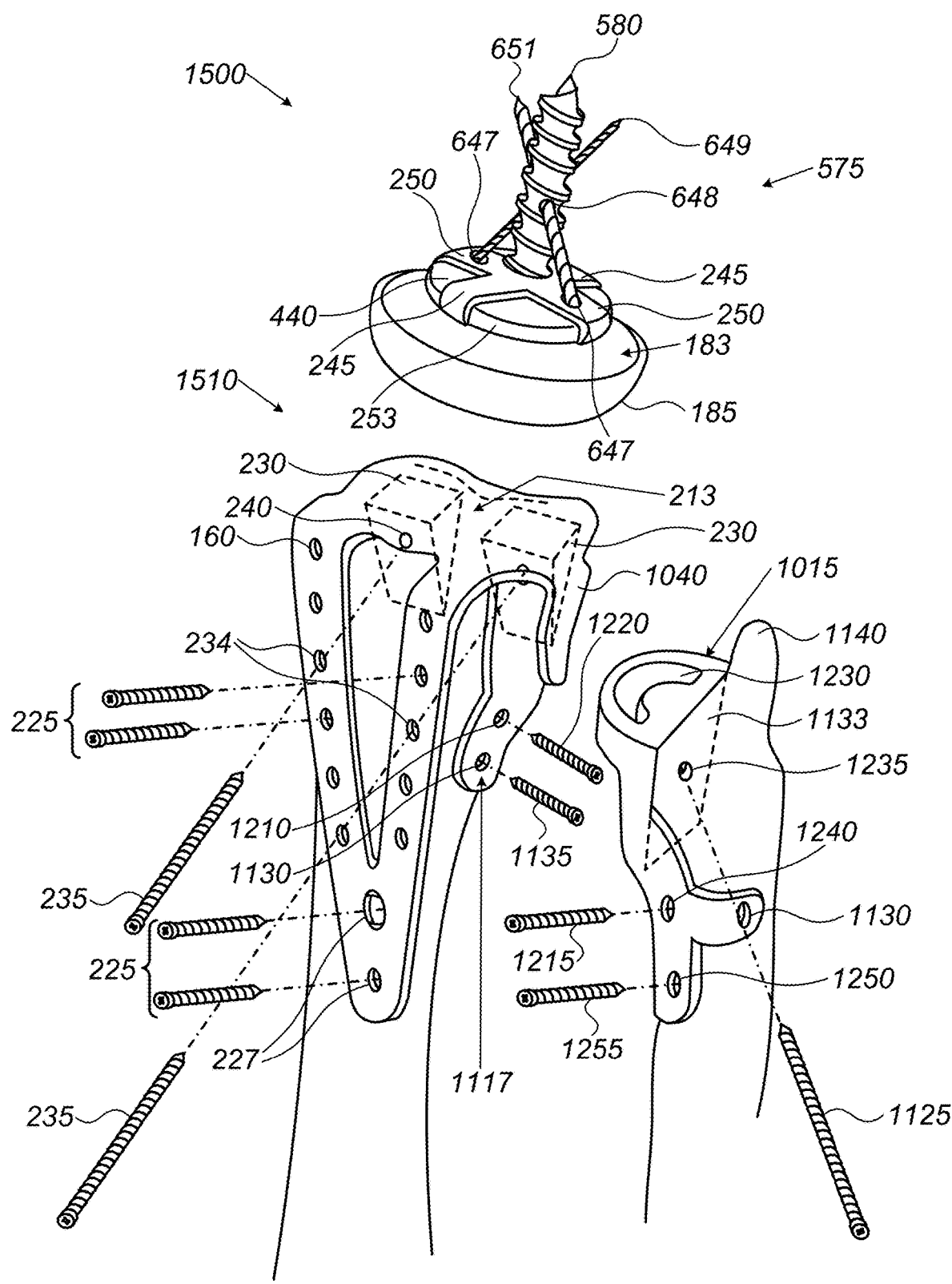
FIG. 16 schematically illustrates an exploded view of a combination of a radiocarpal joint (RCJ) replacement and a distal radioulnar joint (DRUJ) replacement, in accordance with some embodiments of the present invention.

FIG. 16 schematically illustrates an exploded view of combination 1500 of a radiocarpal joint (RCJ) replacement and a distal radioulnar joint (DRUJ) replacement, in accordance with some embodiments of the present invention. A modified radial member 1510 with hook 1040 and lower mounting bracket 1117 of sigmoidal member 1005 is affixed to radial bone 165. Ulnar member 1015 is affixed to ulna bone 170.

After implantation, radial resurfacing plate 213 of modified radial member 1510 with the concave surface is configured to be operably coupled to the convex surface of convex head 185 of carpal capitate member 575 so as to allow radial freedom of motion of the carpal capitate member with respect to the radial resurfacing plate of the RCJ replacement. Hook 1040 is inserted into bore 1230, which is configured to receive and retain the hook. The bore in the DRUJ replacement is shaped to allow relative movements between the radial bone and ulna bone so as to facilitate supination and pronation movement of the wrist. Note that either embodiment of carpal capitate member may be used in the RCJ replacement in FIGS. 15-16 (e.g., carpal capitate member 175 or carpal capitate member 575).

Figure 17A:
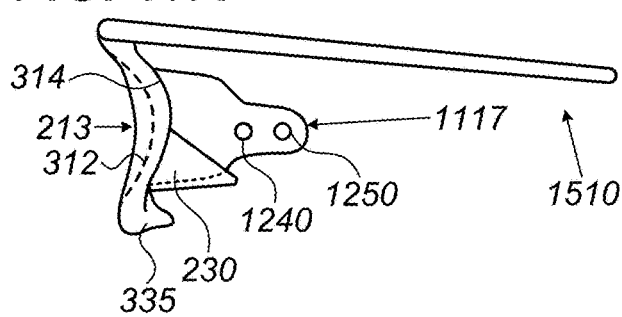
FIG. 17A schematically illustrates a first side view of a modified radial member, in accordance with some embodiments of the present invention.

FIG. 17A schematically illustrates a first side view of modified radial member 1510, in accordance with some embodiments of the present invention.

Figure 17E:
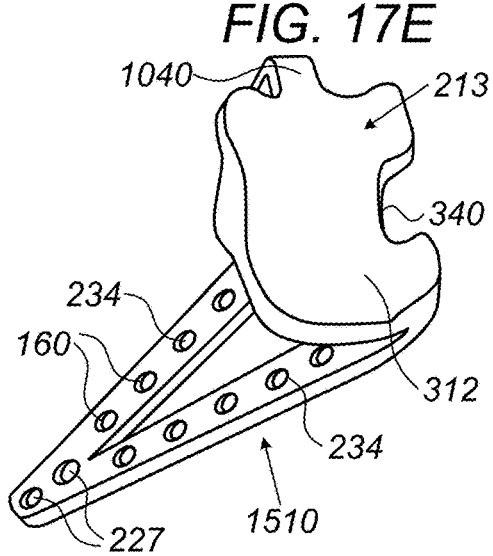
FIG. 17E schematically illustrates a first perspective view of a modified radial member with a hook, in accordance with some embodiments of the present invention.
Figure 17B:
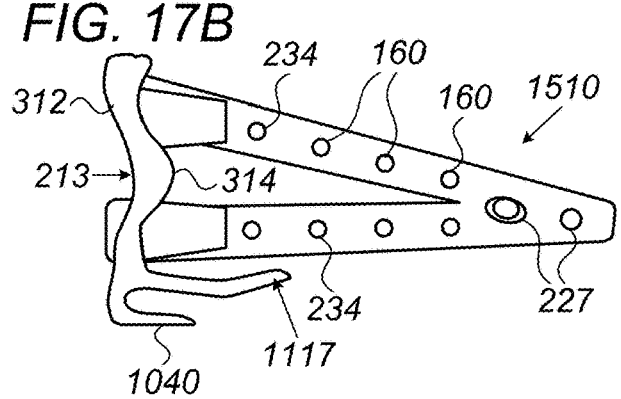
FIG. 17B schematically illustrates a bottom view of a modified radial member with a hook, in accordance with some embodiments of the present invention.

FIG. 17B schematically illustrates a bottom view of modified radial member 1510 with hook 1040, in accordance with some embodiments of the present invention.

Figure 17C:
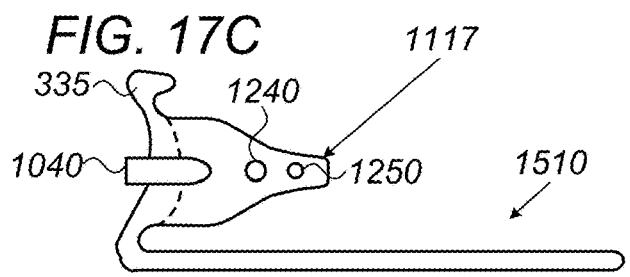
FIG. 17C schematically illustrates a second side view of a modified radial member with a hook, in accordance with some embodiments of the present invention.

FIG. 17C schematically illustrates a second side view of modified radial member 1510 with hook 1040, in accordance with some embodiments of the present invention.

Figure 17D:
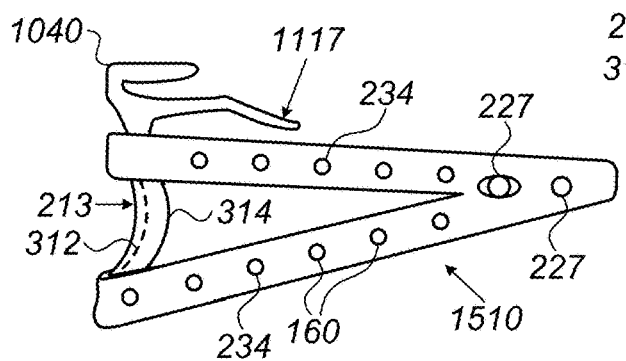
FIG. 17D schematically illustrates a top view of a modified radial member with a hook, in accordance with some embodiments of the present invention.

FIG. 17D schematically illustrates a top view of modified radial member 1510 with hook 1040, in accordance with some embodiments of the present invention.

FIG. 17E schematically illustrates a first perspective view of modified radial member 1510 with hook 1040, in accordance with some embodiments of the present invention.

Figure 17F:
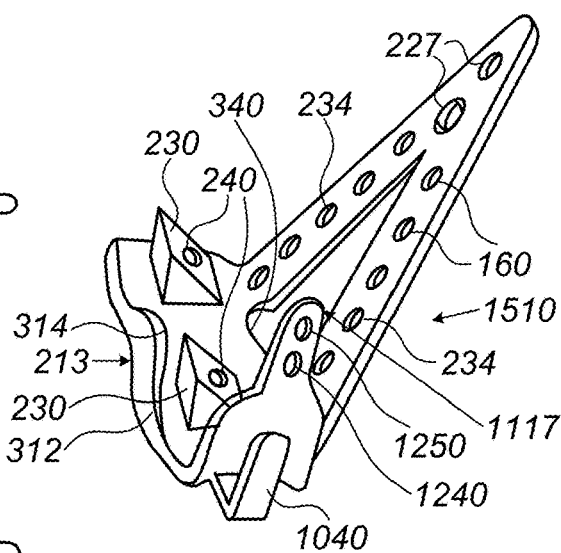
FIG. 17F schematically illustrates a second perspective view of a modified radial member with a hook, in accordance with some embodiments of the present invention.

FIG. 17F schematically illustrates a second perspective view of a modified radial member with hook 1040, in accordance with some embodiments of the present invention.

Modified radial member 1510 is identical to radial member 155 as shown in FIG. 3, with the exception that hook 1040 and lower mounting bracket 1117 from sigmoidal member 1105 are integrally formed in modified radial member 1510.

In accordance with an embodiment of the present invention, a joint replacement device to replace a ball-and-socket joint is configured to provide a required range of motion, e.g., comparable to the range of motion of a replaced joint between two bones, while being capable of withstanding shear and linear forces. The joint includes an azimuthally asymmetric male component that is insertable into an azimuthally asymmetric opening of a female component of the joint. Once inserted into the azimuthally asymmetric opening of the female component, the male component may be rotated about a common axis of the male and female components (e.g., when the joint is unbent) to lock the components together. When the components are locked together, the joint may resist separation of one component from the other when subjected to various shear and linear forces. Articulating surfaces, openings, and necking of the components enables the joint to bend within a range of motion that is compatible with the particular design.

Figure 18A:
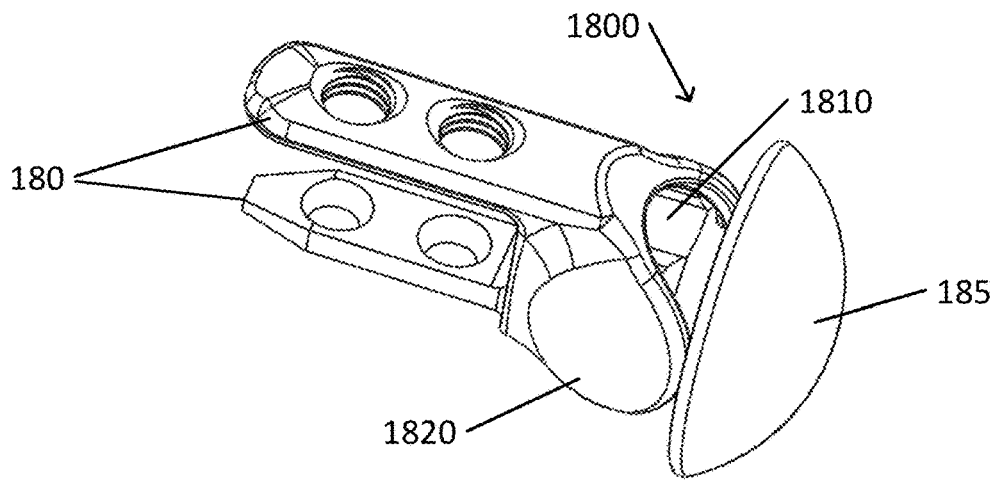
FIG. 18A schematically illustrates a joint replacement device, in accordance with an embodiment of the present invention, when unbent (neutral position)
Figure 18B:
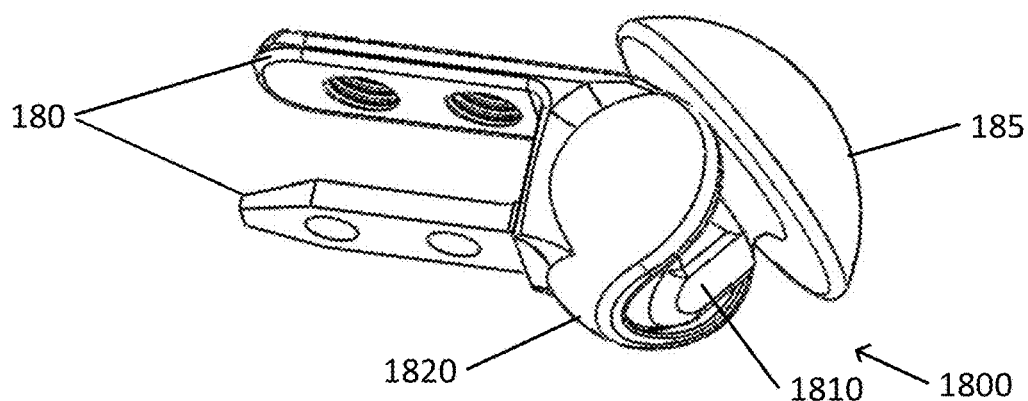
FIG. 18B schematically illustrates the joint replacement device of FIG. 18A when flexed fully upward (fully dorsiflexed or fully extended)
Figure 18C:
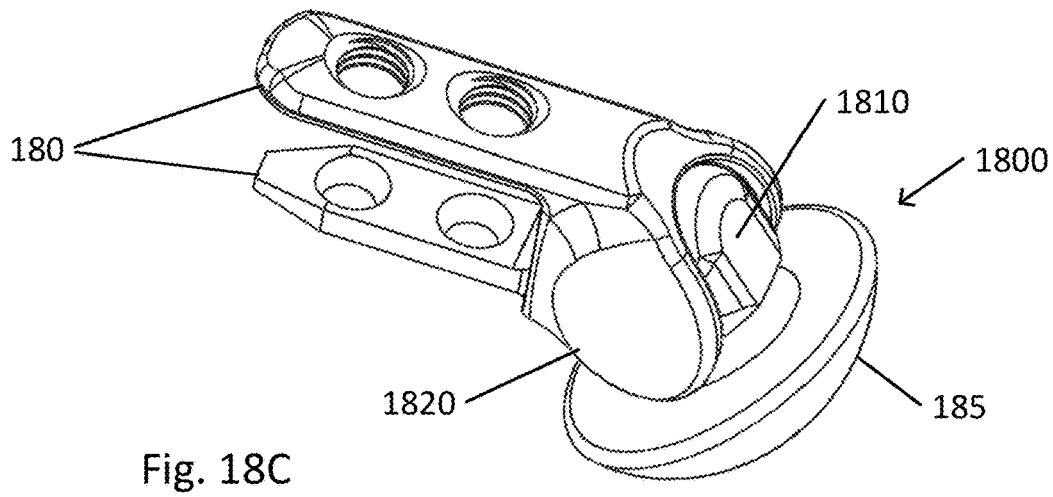
FIG. 18C schematically illustrates the joint replacement device of FIG. 18A when flexed fully downward (fully palmar flexed or fully flexed)

FIG. 18A schematically illustrates a joint replacement device, in accordance with an embodiment of the present invention, when unbent (neutral position). FIG. 18B schematically illustrates the joint replacement device of FIG. 18A when flexed fully upward (fully dorsiflexed or fully extended). FIG. 18C schematically illustrates the joint replacement device of FIG. 18A when flexed fully downward (fully palmar flexed or fully flexed).

Joint replacement device 1800 may be coupled to bones on either side of replaced joint. For example, components of joint replacement device 1800 may be attached directly to the bones, or to structure that is attached to the bones, or may be placed adjacent to bones (e.g., to be held in place by surrounding tissue). In some cases, coupling may include confinement of part of joint replacement device 1800 to the bone or to structure that is attached the bone. For example, in the case of wrist replacement, an end of joint replacement device 1800 may be attached to a bone of the hand, e.g., a carpal capitate member 175, by appropriate structure, e.g., carpal bone insert 180. Similarly, an end of joint replacement device 1800 may be coupled to the forearm, e.g., to a radial articular resurfacing plate that is attached to the radius bone, at convex head 185. (The terms that are included in parentheses in the brief descriptions of FIGS. 18A-18C refer to the corresponding motions of joint replacement device 1800 when replacing a wrist joint.)

Joint replacement device 1800 includes azimuthally asymmetric male component 1810 that is inserted and locked into female component 1820. The structure of male component 1810 and female component 1820 enables a range of motion, partially illustrated by FIGS. 18B and 18C.

Although, in the example shown, convex head 185 is included in azimuthally asymmetric male component 1810, and carpal bone insert 180 is included in female component 1820, other connecting structures that enable attachment to bones of a replaced joint may be included in or attached to each of azimuthally asymmetric male component 1810 and female component 1820.

FIG. 19A schematically illustrates a side view of an azimuthally asymmetric male component of the joint replacement device shown in FIG. 18A, the view showing the long axis of the male component. FIG. 19B schematically illustrates a side view of the azimuthally asymmetric male component shown in FIG. 19A, the view showing the short axis of the male component. FIG. 19C schematically illustrates an axial view of the azimuthally asymmetric male component shown in FIG. 19A.

Azimuthally asymmetric male component 1810 includes outer articulating surface 1904 which is contoured to rotate within a cavity of female component 1820 having a similarly contoured inner surface. In the example shown, outer articulating surface 1904 has the form of a flattened sphere having maximum diameter 1906. In the example shown, opposite sides of outer articulating surface 1904 have been truncated to form side walls 1902. Side walls 1902 are separated by distance 1910, which is shorter than maximum diameter 1906. Although, in the example shown, side walls 1902 are shown as flat, the side walls may be convex, concave, or otherwise curved.

Alternatively to a spherical form, an outer articulating surface of an azimuthally asymmetric male component may have another azimuthally asymmetric form. For example, the outer articulating surface may be in the form of an elongated shape, e.g., a cylinder with rounded (e.g., spherical) end caps, that is mounted such that the long axis of the shape is perpendicular to a longitudinal axis of azimuthally asymmetric male component 1810. Other forms of the outer articulating surface are possible. In general, the transverse perimeter of the outer articulating surface, e.g., when viewed along the longitudinal axis of the azimuthally asymmetric male component (e.g., as in FIG. 19C), is noncircular.

Azimuthally asymmetric male component 1810 is connected to convex head 185 by neck 1908. Neck 1908 narrows to a sufficiently small diameter to enable neck 1908 to travel within an azimuthally asymmetric opening of female component 1820. The travel within the azimuthally asymmetric opening is designed to provide a predetermined range of motion for bending of joint replacement device 1800.

Figure 20A:
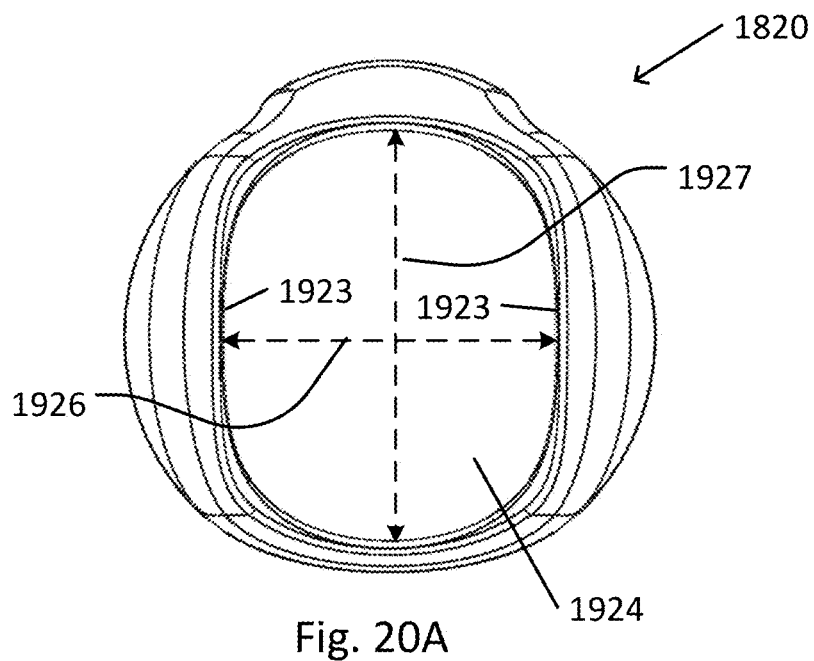
FIG. 20A schematically illustrates a view of an asymmetric opening of the female component of the joint replacement device shown in FIG. 18A.
Figure 20B:
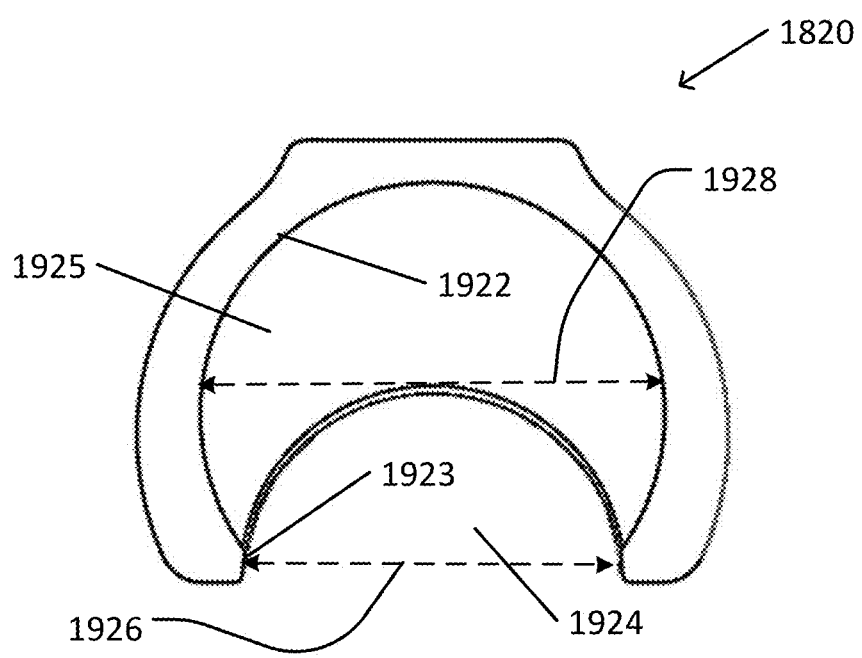
FIG. 20B schematically illustrates a cross section of the female component shown in FIG. 20A, the section parallel to the narrow dimension of the asymmetric opening.

FIG. 20A schematically illustrates a view of an azimuthally asymmetric opening of the female component of the joint replacement device shown in FIG. 18A. FIG. 20B schematically illustrates a cross section of the female component shown in FIG. 20A, the section being parallel to the narrow dimension of the azimuthally asymmetric opening.

Inner articulating surface 1922 of female component 1820, surrounding inner cavity 1925, is shaped similar to outer articulating surface 1904 of azimuthally asymmetric male component 1810. For example, inner articulating surface 1922 may be spherical having a diameter 1928 that is sufficiently larger than maximum diameter 1906 of azimuthally asymmetric male component 1810 to enable azimuthally asymmetric male component 1810 to rotate within inner articulating surface 1922.

Azimuthally asymmetric opening 1924 of female component 1820 is configured to enable insertion of outer articulating surface 1904 when outer articulating surface 1904 is rotated to align with azimuthally asymmetric opening 1924. After insertion of outer articulating surface 1904, rotation of azimuthally asymmetric male component 1810 relative to female component 1820 may cause misalignment between outer articulating surface 1904 and azimuthally asymmetric opening 1924. Azimuthally asymmetric opening 1924 is configured to prevent removal of outer articulating surface 1904 (or insertion) via azimuthally asymmetric opening 1924 when misaligned. For example, azimuthally asymmetric opening 1924 may have a noncircular shape whose dimensions are sufficient close to those of outer articulating surface 1904 to prevent removal of outer articulating surface 1904 when misaligned through a minimum rotation angle. In particular, outer articulating surface 1904 and azimuthally asymmetric opening 1924 may have elongated shapes such that outer articulating surface 1904 may be inserted into azimuthally asymmetric opening 1924 when the long dimensions are aligned (e.g., are mutually parallel), and removal is prevented when no longer aligned. The minimum rotation angle may depend on the dimensions and shapes of outer articulating surface 1904 and azimuthally asymmetric opening 1924.

The minimum rotation angle may be selected to be sufficiently large that movement of the joint is not expected to rotate azimuthally asymmetric male component 1810 or female component 1820 beyond that rotation angle. In some cases, the minimum rotation angle may range from about 10° or less, to about 30°. It may be noted that joint replacement device 1800 is configured to replace a joint where the bones that are joined at the joint are capable of bending relative to one another, but where azimuthal rotation is expected to be minimal.

In the example shown, azimuthally asymmetric opening 1924 has a long dimension whose projected length 1927 (e.g., as viewed head on as in FIG. 20A) is at least as large as maximum diameter 1906 of azimuthally asymmetric male component 1810. In some cases, projected length 1927 may be substantially equal to diameter 1928 of inner cavity 2925. Since diameter 1928 of inner cavity 1925 is typically only slightly larger than maximum diameter 1906, the long dimension of azimuthally asymmetric opening 1924 may extend about halfway about the circumference of inner cavity 1925. The narrower dimension of azimuthally asymmetric opening 1924, indicated by width 1926 between opening sides 1923, is at least slightly wider than distance 1910, but narrower than maximum diameter 1906 of azimuthally asymmetric male component 1810. Thus, when azimuthally asymmetric male component 1810 is oriented such that the direction of distance 1910 is parallel to width 1926, azimuthally asymmetric male component 1810 may be inserted into azimuthally asymmetric opening 1924.

Figure 21A:
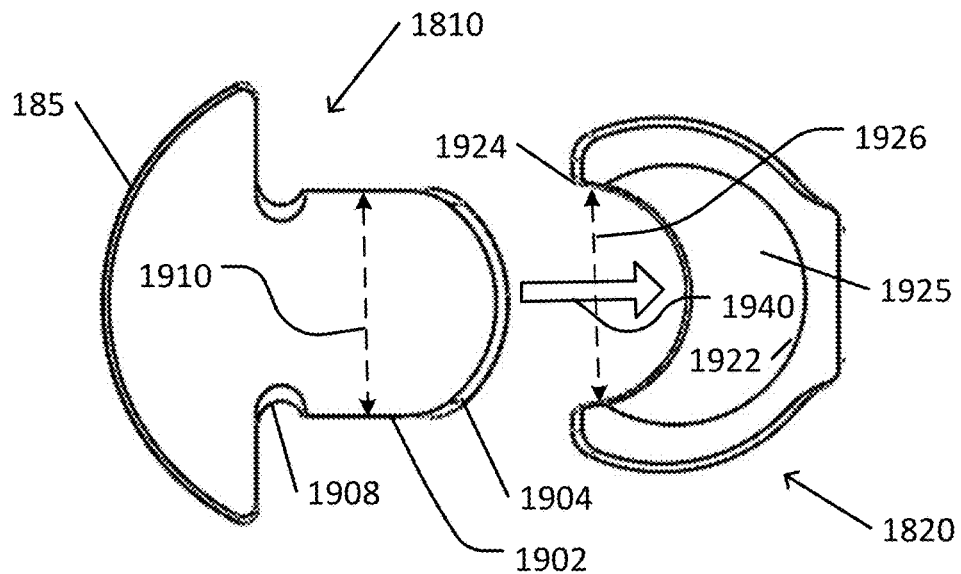
FIG. 21A schematically illustrates insertion of the asymmetric male component of the joint replacement device shown in FIG. 18A into the asymmetric opening of the female component.

FIG. 21A schematically illustrates insertion of the azimuthally asymmetric male component of the joint replacement device shown in FIG. 18A into the azimuthally asymmetric opening of the female component.

In order for azimuthally asymmetric male component 1810 to be inserted into azimuthally asymmetric opening 1924 to assemble joint replacement device 1800, distance 1910 between side walls 1902 of azimuthally asymmetric male component 1810 may be aligned with width 1926 of azimuthally asymmetric opening 1924 of female component 1820 (equivalent to side walls 1902 being aligned with sides 1923) Similarly, the maximum diameter 1906 that is perpendicular to the direction of distance 1910 may be aligned with the long dimension of azimuthally asymmetric opening 1924 (diameter 1928).

When so oriented, azimuthally asymmetric male component 1810 may be inserted with insertion movement 1940 through azimuthally asymmetric opening 1924 of female component 1820 into inner cavity 1925 of female component 1820.

Figure 21B:
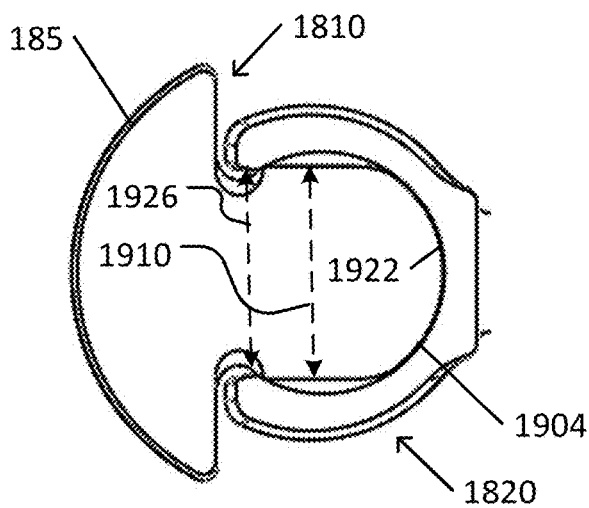
FIG. 21B schematically illustrates the asymmetric male component of FIG. 21A fully inserted into the asymmetric opening of the female component.

FIG. 21B schematically illustrates the azimuthally asymmetric male component of FIG. 21A fully inserted into the azimuthally asymmetric opening of the female component.

When azimuthally asymmetric male component 1810 is fully inserted into female component 1820, outer articulating surface 1904 of azimuthally asymmetric male component 1810 is adjacent to inner articulating surface 1922 of inner cavity 1925 of female component 1820.

Figure 21C:
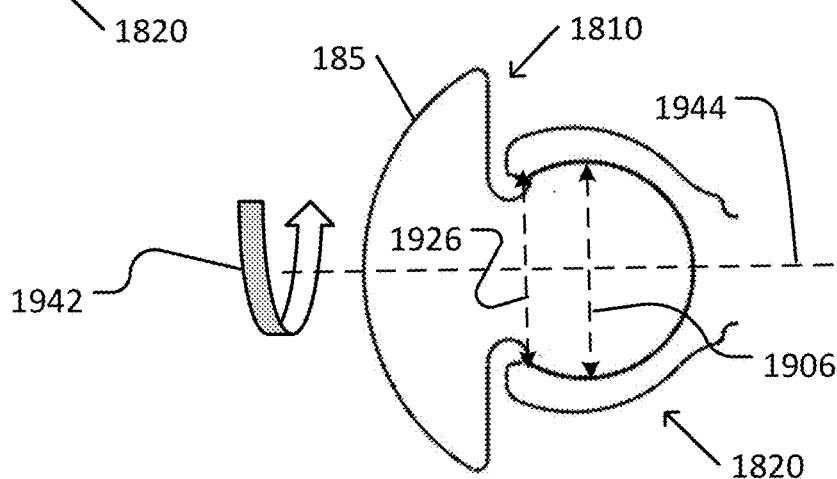
FIG. 21C schematically illustrates rotation of the asymmetric male component of FIG. 21B to lock the male component into the asymmetric opening to form the joint replacement device shown in FIG. 18A.

FIG. 21C schematically illustrates rotation of the azimuthally asymmetric male component of FIG. 21B to lock the male component into the azimuthally asymmetric opening to form the joint replacement device shown in FIG. 18A.

Inserted azimuthally asymmetric male component 1810 may be rotated with rotation motion 1942 (or in the opposite direction) about longitudinal axis 1944. As a result of rotation motion 1942, maximum diameter 1906 of azimuthally asymmetric male component 1810 may no longer be aligned with the long dimension of azimuthally asymmetric opening 1924 (diameter 1928). With this rotation, azimuthally asymmetric male component 1810 can no longer be removed from inner cavity 1925 via azimuthally asymmetric opening 1924. In particular, when rotated through about 90°, maximum diameter 1906 of azimuthally asymmetric male component 1810 may be aligned with width 1926 of azimuthally asymmetric opening 1924. Thus, azimuthally asymmetric male component 1810 and female component 1820 may be locked together to form joint replacement device 1800. A minimum rotation angle for locking together azimuthally asymmetric male component 1810 and female component 1820 may depend on the shape and dimensions of azimuthally asymmetric male component 1810 and of azimuthally asymmetric opening 1924, as well on the surrounding anatomy and expected motions of the bones and tissue in the vicinity of joint replacement device 1800.

When azimuthally asymmetric male component 1810 and female component 1820 are locked together, azimuthally asymmetric opening 1924 may prevent azimuthally asymmetric male component 1810 from being pulled out of female component 1820 by a stretching force (e.g., a tension exerted on joint replacement device 1800 approximately parallel to longitudinal axis 1944). The close fit between outer articulating surface 1904 of azimuthally asymmetric male component 1810 and inner articulating surface 1922 of inner cavity 1925 of female component 1820 may resist shear forces that are applied to joint replacement device 1800 (e.g., along a direction approximately perpendicular to longitudinal axis 1944).

When azimuthally asymmetric male component 1810 and female component 1820 are locked together, neck 1908 may be located within azimuthally asymmetric opening 1924. Rotation of asymmetric male component 1810 relative to female component 1820 may cause neck 1908 to travel within azimuthally asymmetric opening 1924. The rotation may thus be limited by the dimensions of neck 1908 and of travel within azimuthally asymmetric opening 1924.

In the example shown, travel of neck 1908 along the length of azimuthally asymmetric opening 1924 may provide flexion-extension bending for a replaced wrist joint.

Figure 22A:
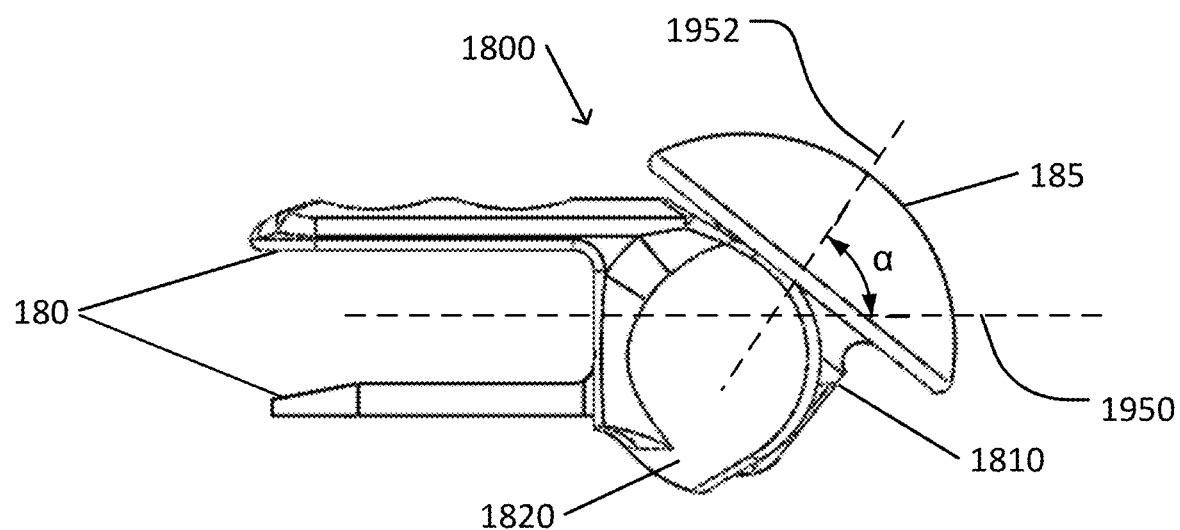
FIG. 22A schematically illustrates range of motion of the joint replacement device shown in FIG. 18A for bending parallel to the length of the asymmetric opening.

FIG. 22A schematically illustrates range of motion of the joint replacement device shown in FIG. 18A for bending parallel to the length of the azimuthally asymmetric opening.

The range of motion for longitudinal bending parallel to the long dimension of azimuthally asymmetric opening may depend on the actual length of azimuthally asymmetric opening 1924 and on the diameter of neck 1908. The range may be defined by the angle $\alpha$ between female component axis 1950 of female component 1820 and male component axis 1952 of azimuthally asymmetric male component 1810 at maximum bending in one direction. If azimuthally asymmetric opening 1924 is symmetrically arranged about female component axis 1950, the range for bending in the opposite direction will also be $\alpha$. Therefore, the range of motion for the longitudinal bending may be $\pm\alpha$. For example, when joint replacement device 1800 replaces a wrist joint, $\pm\alpha$ may be typically less then the typical range of motion for flexion-extension bending of a healthy wrist joint (about $\pm 90°$)

Typically, the diameter of neck 1908 is less than width 1926 of azimuthally asymmetric opening 1924. Therefore, neck 1908 may travel laterally within azimuthally asymmetric opening 1924 parallel to the dimension of width 1926. For example, this lateral travel may provide lateral ulnar-radial bending of a replaced wrist joint.

Figure 22B:
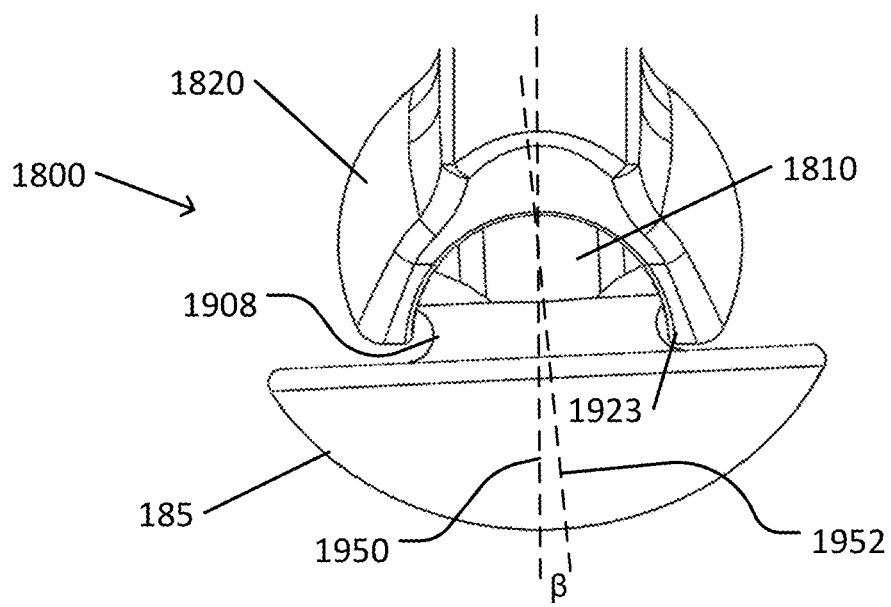
FIG. 22B schematically illustrates range of motion of the joint replacement device shown in FIG. 18A for bending perpendicular to the length of the asymmetric opening.

FIG. 22B schematically illustrates range of motion of the joint replacement device shown in FIG. 18A for bending perpendicular to the length of the azimuthally asymmetric opening.

The range of motion for lateral bending parallel to width 1926, the narrow dimension of azimuthally asymmetric opening 1924, may be limited by contact of neck 1908 with opening sides 1923 of azimuthally asymmetric opening 1924. The value of the range of motion may thus depend on the sizes of width 1926 and of the diameter of neck 1908. The range may be defined by the angle (3 between female component axis 1950 of female component 1820 and male component axis 1952 of azimuthally asymmetric male component 1810 at maximum bending in one lateral direction. If width 1926 of azimuthally asymmetric opening 1924 is symmetrically arranged about female component axis 1950, the range for bending in the opposite direction will also be $\beta$. Therefore, the range of motion for the longitudinal bending may be $\pm\beta$. Typically, $\pm\beta$ may be less then the typical range of motion for lateral ulnar-radial bending of a healthy wrist joint (typically between about $\pm 20°$ and $\pm 30°$).

Different embodiments are disclosed herein. Features of certain embodiments may be combined with features of other embodiments; thus, certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A joint replacement device comprising:
   an azimuthally asymmetric male component configured to couple, directly to a bone or to a structure that is attached to the bone, on one side of a joint between two bones, the azimuthally asymmetric male component comprising an outer articulating surface having a neck; and
   a female component configured to couple to a bone on an opposite side of the joint between the two bones, the female component comprising a cavity, wherein the female component comprises an inner articulating surface surrounding the cavity and configured to enable the outer articulating surface of the male component to rotate within the cavity, the cavity comprising an azimuthally asymmetric opening that is shaped to enable insertion of the outer articulating surface into the cavity through the opening when the outer articulating surface is aligned with the opening, and to prevent separation of the male component from the female component when the inserted outer articulating surface is rotated such that the outer articulating surface is not aligned with the opening,
   wherein, after insertion of the outer articulating surface into the cavity, the neck is located within the opening and the outer articulating surface is rotatable within the inner articulating surface with a rotation that is limited by dimensions of the opening and the neck.

2. The device of claim 1, wherein the outer articulating surface and the opening are each elongated, and the outer articulating surface and the opening are aligned when a long dimension of the outer articulating surface is parallel to a long dimension of the opening.

3. The device of claim 2, wherein a diameter of the neck is selected to provide a predetermined range of motion of the replacement joint for longitudinal bending parallel to the long dimension of the opening.

4. The device of claim 2, wherein a width of the opening and a diameter of the neck are selected to provide a predetermined range of motion of the replacement joint for lateral bending parallel to the width of the opening.

5. The device of claim 2, wherein the outer articulating surface is substantially spherical with flattened opposite sides.

6. The device of claim 5, wherein a projected length of the opening is longer than a diameter of the of the outer articulating surface.

7. The device of claim 6, wherein a projected length of the opening is substantially equal to a diameter of the inner articulating surface.

8. The replacement joint of claim 1, wherein the replacement joint is a wrist replacement joint.

9. The device of claim 8, wherein the structure that is attached to the male component comprises a convex head.

10. The device of claim 8, wherein the female member includes a carpal bone insert for attaching to a carpal capitate member.

* * * * *